(12) United States Patent
Zhang

(10) Patent No.: US 7,567,836 B2
(45) Date of Patent: Jul. 28, 2009

(54) ECG SIGNAL POWER VECTOR DETECTION OF ISCHEMIA OR INFARCTION

(75) Inventor: Yi Zhang, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 287 days.

(21) Appl. No.: 11/275,800

(22) Filed: Jan. 30, 2006

(65) Prior Publication Data

US 2007/0179392 A1    Aug. 2, 2007

(51) Int. Cl.
A61B 5/0452    (2006.01)
(52) U.S. Cl. .......................... 600/512; 600/516; 600/517
(58) Field of Classification Search ................. 600/508, 600/512, 517
See application file for complete search history.

(56) References Cited

U.S. PATENT DOCUMENTS

| | | | |
|---|---|---|---|
| 4,686,987 A | 8/1987 | Salo et al. |
| 4,905,706 A | 3/1990 | Duff et al. |
| 4,967,760 A | 11/1990 | Bennett et al. |
| 5,040,533 A | 8/1991 | Fearnot |
| 5,127,401 A | 7/1992 | Grevious et al. |
| 5,174,289 A | 12/1992 | Cohen |
| 5,190,035 A | 3/1993 | Salo et al. |
| 5,267,560 A | 12/1993 | Cohen |
| 5,301,679 A | 4/1994 | Taylor |
| 5,337,752 A | 8/1994 | Reeves |
| 5,472,453 A | 12/1995 | Alt |
| 5,554,177 A | 9/1996 | Kieval et al. |
| 5,593,431 A | 1/1997 | Sheldon |
| 5,626,620 A | 5/1997 | Kieval et al. |
| 5,628,777 A | 5/1997 | Moberg et al. |
| 5,687,738 A | 11/1997 | Shapiro et al. |
| 5,700,283 A | 12/1997 | Salo |

(Continued)

FOREIGN PATENT DOCUMENTS

JP    2000-316825    11/2000

(Continued)

OTHER PUBLICATIONS

"U.S. Appl. No. 10/795,126 Non final office action mailed Jan. 25, 2007", 17 pgs.

(Continued)

*Primary Examiner*—Carl H Layno
*Assistant Examiner*—Gary A Porter, Jr.
(74) *Attorney, Agent, or Firm*—Schwegman, Lundberg & Woessner, P.A.

(57) ABSTRACT

A system comprising a processor that includes a cardiac signal vector module and an ischemia detection module. The cardiac signal vector module is configured to measure a first dominant vector corresponding to a direction and magnitude of maximum signal power of a first segment of at least one cardiac cycle of a subject and at least a second dominant vector corresponding to a direction and magnitude of maximum signal power of a second segment of the cardiac cycle from an electrical cardiac signal. The ischemia detection module is configured to measure a change in the first dominant vector, to form a difference by subtracting a measured change in the second dominant vector from a measured change in the first dominant vector, and to declare whether an ischemic event occurred using the difference.

20 Claims, 16 Drawing Sheets

U.S. PATENT DOCUMENTS

| | | | |
|---|---|---|---|
| 5,725,562 A | 3/1998 | Sheldon | |
| 5,803,084 A | 9/1998 | Olson | |
| 5,824,019 A | 10/1998 | Rueter et al. | |
| 5,860,933 A | 1/1999 | Don Michael | |
| 5,935,081 A | 8/1999 | Kadhiresan | |
| 6,009,349 A | 12/1999 | Mouchawar et al. | |
| 6,044,297 A | 3/2000 | Sheldon et al. | |
| 6,076,014 A | 6/2000 | Alt | |
| 6,104,949 A | 8/2000 | Pitts Crick et al. | |
| 6,115,628 A * | 9/2000 | Stadler et al. | 600/517 |
| 6,115,630 A | 9/2000 | Stadler et al. | |
| 6,128,526 A | 10/2000 | Stadler et al. | |
| 6,179,865 B1 | 1/2001 | Hsu et al. | |
| 6,193,668 B1 | 2/2001 | Chassaing et al. | |
| 6,285,898 B1 | 9/2001 | Ben-Haim | |
| 6,324,421 B1 | 11/2001 | Stadler et al. | |
| 6,361,522 B1 | 3/2002 | Scheiner et al. | |
| 6,368,284 B1 | 4/2002 | Bardy | |
| 6,381,493 B1 | 4/2002 | Stadler et al. | |
| 6,397,100 B2 | 5/2002 | Stadler et al. | |
| 6,400,981 B1 | 6/2002 | Govari | |
| 6,466,821 B1 | 10/2002 | Pianca et al. | |
| 6,478,746 B2 | 11/2002 | Chassaing et al. | |
| 6,496,715 B1 | 12/2002 | Lee et al. | |
| 6,505,067 B1 | 1/2003 | Lee et al. | |
| 6,522,917 B1 | 2/2003 | Hsu et al. | |
| 6,522,923 B1 | 2/2003 | Turcott | |
| 6,526,313 B2 | 2/2003 | Sweeney et al. | |
| 6,625,493 B2 | 9/2003 | Kroll et al. | |
| 6,658,283 B1 | 12/2003 | Bornzin et al. | |
| 6,658,292 B2 | 12/2003 | Kroll et al. | |
| 6,719,701 B2 | 4/2004 | Lade | |
| 7,299,086 B2 | 11/2007 | McCabe et al. | |
| 2002/0016548 A1 | 2/2002 | Stadler et al. | |
| 2002/0143262 A1* | 10/2002 | Bardy | 600/508 |
| 2003/0013974 A1 | 1/2003 | Natarajan et al. | |
| 2003/0040676 A1 | 2/2003 | Prentice et al. | |
| 2003/0045805 A1 | 3/2003 | Sheldon et al. | |
| 2003/0083586 A1 | 5/2003 | Ferek-Petric | |
| 2003/0105496 A1 | 6/2003 | Yu et al. | |
| 2004/0015090 A1 | 1/2004 | Sweeney et al. | |
| 2004/0106960 A1 | 6/2004 | Siejko et al. | |
| 2004/0106961 A1 | 6/2004 | Siejko et al. | |
| 2004/0106962 A1 | 6/2004 | Mai et al. | |
| 2004/0127792 A1 | 7/2004 | Siejko et al. | |
| 2004/0215264 A1 | 10/2004 | Van Bentem | |
| 2005/0148896 A1 | 7/2005 | Siejko et al. | |
| 2005/0149136 A1 | 7/2005 | Siejko et al. | |
| 2005/0197674 A1 | 9/2005 | McCabe et al. | |
| 2006/0025699 A1 | 2/2006 | Maile et al. | |
| 2006/0095083 A1 | 5/2006 | Zhang et al. | |
| 2006/0161070 A1 | 7/2006 | Siejko et al. | |
| 2007/0167849 A1 | 7/2007 | Zhang et al. | |
| 2007/0179392 A1 | 8/2007 | Zhang | |
| 2008/0051672 A1 | 2/2008 | McCabe et al. | |

FOREIGN PATENT DOCUMENTS

| | | |
|---|---|---|
| WO | WO-02/087694 | 11/2002 |
| WO | WO-03041797 A2 | 5/2003 |
| WO | WO-2005089643 A1 | 9/2005 |
| WO | WO-2006078757 A1 | 7/2006 |

OTHER PUBLICATIONS

"U.S. Appl. No. 10/795,126 Notice of allowance mailed Jul. 9, 2007", 10 pgs.

"U.S. Appl. No. 10/795,126 Response filed Apr. 25, 2007 to Non final office action mailed Jan. 25, 2007", 11 pgs.

"U.S. Appl. No. 10/900,570 Response filed Apr. 10, 2008 to Non-Final Office Action mailed Jan. 10, 2008", 7 pgs.

"U.S. Appl. No. 10/975,166 Notice of allowance mailed Dec. 21, 2006", 17 pgs.

"U.S. Appl. No. 11/037,275 Final Office Action mailed Jun. 17, 2008", 13 pgs.

"U.S. Appl. No. 11/037,275, Non-Final Office Action mailed Dec. 12, 2007", 17 pgs.

"U.S. Appl. No. 11/037,278 Response filed Sep. 17, 2008 to Final Office Action mailed Jun. 17, 2008", 12 pgs.

"U.S. Appl. No. 11/135,985 Notice of Allowance mailed Apr. 25, 2008", 4 pgs.

"U.S. Appl. No. 11/135,985 Non-Final Office Action Mailed Sep. 25, 2007", 11 pgs.

"U.S. Appl. No. 10/900,570, Non-Final Office Action mailed Jan. 10, 2008", 4 pgs.

"U.S. Appl. No. 10/900,570, Non-Final Action mailed Jul. 25, 2008", 5 pgs.

"International Search Report and Written Opinion for Application No. PCT/US2006/001801, date mailed Jun. 16, 2006", 12 pgs.

"Screenshots taken of Display of Model 2920 Programmer, Using Model 2845 Software Application", *Guidant Corporation*, Effective Date of First Use: Dec. 2, 1999. See e-mail in matter management, 5 pgs.

Auricchio, Angelo, et al., "Dynamically Optimized Multisite Cardiac Resynchronization Device", U.S. Appl. No. 10/071,875, filed Feb. 8, 2002, 22 pgs.

Brockway, Marina, et al., "Method and Apparatus for Optimization of Cardiac Resynchronization Therapy Using Heart Sounds", U.S. Appl. No. 10/865,498, filed Jun. 10, 2004, 45 pgs.

Maile, Keith R., et al., "A Dual-Use Sensor for Rate Responsive Pacing and Heart Sound Monitoring", U.S. Appl. No. 10/703,175, filed Nov. 6, 2003, 41 pgs.

Maile, Keith R., et al., "Determining a Patient's Posture From Mechanical Vibrations of the Heart", U.S Appl. No. 10/900,570, filed Jul. 28, 2004, 24 pgs.

Pastore, Joseph M, et al., "Method And Apparatus For Detecting Acoustic Oscillations In Cardiac Rythm", U.S. Appl. No. 10/138,046, filed May 3, 2002, 25 pgs.

Pastore, Joseph M, "Method And Apparatus For Detecting Oscillation In Cardiac Rhythm", U.S. Appl. No. 10/172,825, filed Jun. 14, 2002, 33 pgs.

Prinzen, Frits W, "Mapping of regional myocardial strain and work during ventricular pacing: experimental study using magnetic resonance imaging tagging", *Journal of the American College of Cardiology*, 33(6), (May, 1999), 1735-1742.

Siejko, K. Z., et al., "Method for Correction of Posture Dependence on Heart Sounds", U.S. Appl. No. 11/037,275, filed Jan. 18, 2005, 26 pgs.

Siejko, Krzysztof Z., "A Third Heart Sound Activity Index for Heart Failure Monitoring", U.S. Appl. No. 10/746,874, filed Dec. 24, 2003, 41 pgs.

Siejko, Krzysztof Z., et al., "Method and Apparatus for Third Heart Sound Detection", U.S. Appl. No. 10/746,853, filed Dec. 24, 2003, 40 pgs.

Stein, Emanuel, et al., "Rapid Interpretation of Heart Sounds and Murmurs", *Baltimore: Williams & Wilkins, 4th ed.*, (1997), 85-105.

Woldbaek, Per Reidar, et al., "Increased cardiac IL-18 mRNA, pro-IL-18 and plasma IL-18 after myocardial infarction in the mouse; a potential role in cardiac dysfunction", *Cardiovascular Research*, 59, (2003), 122-131.

Zhang, Y., et al., "Ischemia Detection Using a Heart Sound Sensor", U.S. Appl. No. 11/148,107, filed Jun. 8, 2005, 41 pgs.

* cited by examiner

BASELINE

ISCHEMIA

ECG SIGNAL POWER VECTOR DETECTION OF ISCHEMIA OR INFARCTION

CROSS REFERENCE TO RELATED APPLICATIONS

This application is related to the following co-pending, commonly assigned U.S. patent application Ser. No. 11/124,950, entitled "POSTURE MONITORING USING CARDIAC ACTIVATION SEQUENCES," filed on May 9, 2005, and U.S. Provisional Patent Application Ser. No. 60/631,742 entitled "CARDIAC ACTIVATION SEQUENCE MONITORING FOR ISCHEMIA DETECTION,", filed on Nov. 30, 2004, each of which is hereby incorporated by reference.

TECHNICAL FIELD

The field generally relates to implantable medical devices and, in particular, but not by way of limitation, to systems and methods for monitoring electrical activity of the heart.

BACKGROUND

Implantable medical devices (IMDS) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy and to aid a physician or caregiver in patient diagnosis through internal monitoring of a patient's condition. The devices may include one or more electrodes in communication with sense amplifiers to monitor electrical heart activity within a patient, and often include one or more sensors to monitor one or more other internal patient parameters. Other examples of implantable medical devices include implantable diagnostic devices, implantable insulin pumps, devices implanted to administer drugs to a patient, or implantable devices with neural stimulation capability.

Additionally, some IMDs detect events by monitoring electrical heart activity signals. In CFM devices, these events include heart chamber expansions or contractions. Ischemia occurs when not enough blood reaches the tissue of the heart. Detecting ischemia early is critical to the health of the patient. Because of the damaged tissue, heart depolarization becomes altered and an ischemic episode may be manifested in the electrical signals.

SUMMARY

This document discusses, among other things, systems and methods for monitoring electrical activity of the heart. A system example includes a processor that in turn includes a cardiac signal vector module and an ischemia detection module. The cardiac signal vector module is configured to measure a first dominant vector corresponding to a direction and magnitude of maximum signal power of a first segment of at least one cardiac cycle of a subject and at least a second dominant vector corresponding to a direction and magnitude of maximum signal power of a second segment of the cardiac cycle from an electrical cardiac signal. The ischemia detection module is configured to measure a change in the first dominant vector, to form a difference by subtracting a measured change in the second dominant vector from the measurement of the change in the first dominant vector, and to declare whether an ischemic event occurred using the difference.

A method embodiment includes sensing at least one cardiac signal representative of cardiac activity of a subject using an implantable medical device (IMD), calculating a first dominant vector corresponding to a direction and magnitude of maximum signal power of a first segment of a cardiac cycle and a second dominant vector corresponding to a direction and magnitude of maximum signal power of a second segment of a cardiac cycle from the cardiac signal, measuring a change in the first dominant vector, measuring a change in the second dominant vector, and subtracting the change in the second dominant vector from the measured change in the first dominant signal vector to form a difference.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

Figure 1A:
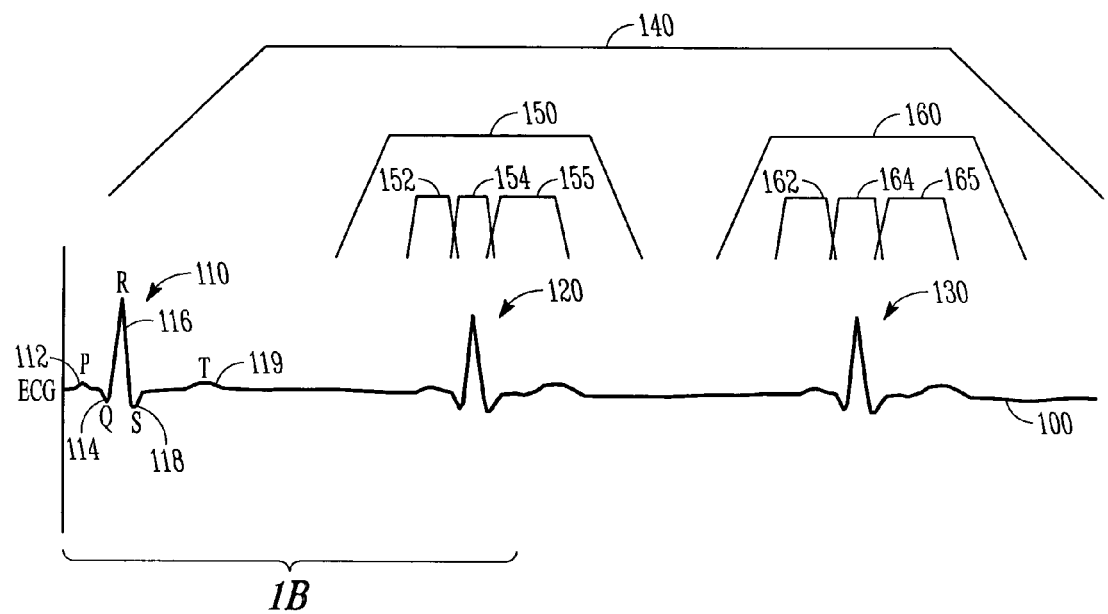
FIGS. 1A and 1B illustrate an ECG waveform.

In the following detailed description, reference is made to the accompanying drawings which form a part hereof, and specific embodiments in which the invention may be practiced are shown by way of illustration. It is to be understood that other embodiments may be used and structural or logical changes may be made without departing from the scope of the present invention.

The functions or algorithms described herein are typically implemented in software or a combination of software and human implemented procedures in one embodiment. The software typically comprises computer executable instructions stored on computer readable media such as memory or other type of storage devices. The term "computer readable media" is also used to represent carrier waves on which the software is transmitted. Further, such functions typically correspond to modules, which are software, hardware, firmware or any combination thereof. Multiple functions are performed in one or more modules as desired, and the embodiments described are merely examples. The software is typically executed on a digital signal processor, application specific integrated circuit (ASIC), microprocessor, or other type of processor. The processor may operate as part of an implantable medical device or the processor may operate on a computer system, such as a personal computer, server or other computer system.

An implantable medical device may include one or more of the features, structures, methods, or combinations thereof described herein. For example, a cardiac monitor or a cardiac stimulator may be implemented to include one or more of the advantageous features and/or processes described below. It is intended that such a monitor, stimulator, or other implantable or partially implantable device need not include all of the features described herein, but may be implemented to include selected features that provide for unique structures and/or functionality. Such a device may be implemented to provide a variety of therapeutic or diagnostic functions.

A wide variety of implantable cardiac monitoring and/or stimulation devices may be configured to implement a cardiac activation sequence monitoring and/or tracking methodology. A non-limiting, representative list of such devices includes cardiac monitors, pacemakers, cardiovertors, defibrillators, resynchronizers, and other cardiac monitoring and therapy delivery devices, including cardiac devices that include or work in coordination with neuro-stimulating devices, drug pumps, or other therapies. These devices may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes). Monitoring of electrical signals related to cardiac activity may provide early, if not immediate, diagnosis of ischemia. The present inventors have recognized a need for improved sensing of events related to cardiac activity.

Method and system examples described herein reject noise in cardiac signal separation methodologies. Signal separation methodologies separate composite signals into signals from individual sources. Composite cardiac signals typically are sensed using multiple implantable electrodes. Signal separation is used to produce one or more cardiac activation signal vectors associated with one or more cardiac activation sequences. A change in the signal vector may be detected using subsequent separations. The change may be used to diagnose, detect, predict, quantify, and/or qualify an event such as ischemia, an arrhythmia, a myocardial infarction, or other pathologic change. Information associated with the vectors may be stored and used to track the vectors. As an illustrative example, one component of noise in such measurements is noise due to postural changes of a patient or subject. Rejecting the noise due to posture changes of a patient may improve specificity of ischemic detection by reducing false positives.

The examples may be implemented in the context of a wide variety of cardiac devices, such as those listed above, and are referred to herein generally as implantable medical devices (IMD) for convenience. An IMD may incorporate one or more of the electrode types identified above and/or combinations thereof.

Cardiac activation sequence monitoring and/or tracking systems may employ more than two electrodes of varying location, and possibly of varying configuration. In one embodiment, for example, two or more electrodes may conveniently be located on the IMD header, whereas the hermetically sealed canister or "can" of the IMD itself may be the third electrode. In another embodiment, one electrode may be located on the IMD header, another is the can electrode, and a third may be an IMD antenna used for radio frequency (RF) telemetry.

Electrocardiogram (ECG) signals originate from electrophysiological signals originating in and propagated through the cardiac tissue, which provide for the cardiac muscle contraction that pumps blood through the body. A sensed ECG signal is effectively a superposition of all the depolarizations occurring within the heart that are associated with cardiac contraction, along with noise components. The propagation of the depolarizations through the heart may be referred to as a depolarization wavefront. The sequence of depolarization wavefront propagation through the chambers of the heart, providing the sequential timing of the heart's pumping, is designated an activation sequence.

ECG signals are sensed using one or more ECG sensing circuits. Examples of ECG sensing circuits include surface ECG circuits, subcutaneous ECG circuits, intracardiac electrogram (EGM) sensing circuits, and wireless ECG circuits. In a surface ECG sensing circuit, electrodes are placed on a subject's skin. In a subcutaneous ECG sensing circuit, electrodes are implanted just beneath the skin and the ECG signal obtained is referred to as subcutaneous ECG or far-field electrogram. In an intracardiac EGM circuit and in a wireless ECG circuit, at least one electrode is placed in or around the heart. A wireless ECG includes a plurality of electrodes to provide differential sensing of cardiac signals to approximate a surface ECG. Descriptions of wireless ECG systems are found in commonly assigned, co-pending U.S. patent application Ser. No. 10/795,126 by McCabe et al., entitled "Wireless ECG in Implantable Devices," filed on Mar. 5, 2004, which is incorporated herein by reference.

A signal separation technique may be implemented to separate activation sequence components of ECG signals, and to produce one or more cardiac signal vectors associated with all or a portion of one or more cardiac activation sequences based on the separation. The activation sequence components may be viewed as the signal sources that make up the ECG signals, and the signal separation process may be referred to as a source separation process or simply source separation. One illustrative signal source separation methodology useful for producing cardiac signal vectors associated with cardiac activation sequences is designated blind source separation, which will be described in further detail below.

In general, the quality of the electrocardiogram or electrogram sensed from one pair of electrodes of an IMD depends on the orientation of the electrodes with respect to the depolarization wavefront produced by the heart. The signal sensed on an electrode bipole is the projection of the ECG vector in the direction of the bipole. Cardiac activation sequence monitoring and/or tracking algorithms described herein advantageously exploit the strong correlation of signals from a common origin (the heart) across spatially distributed electrodes, such as to detect, monitor, and/or track the activation sequence for posture monitoring.

Figure 1B:
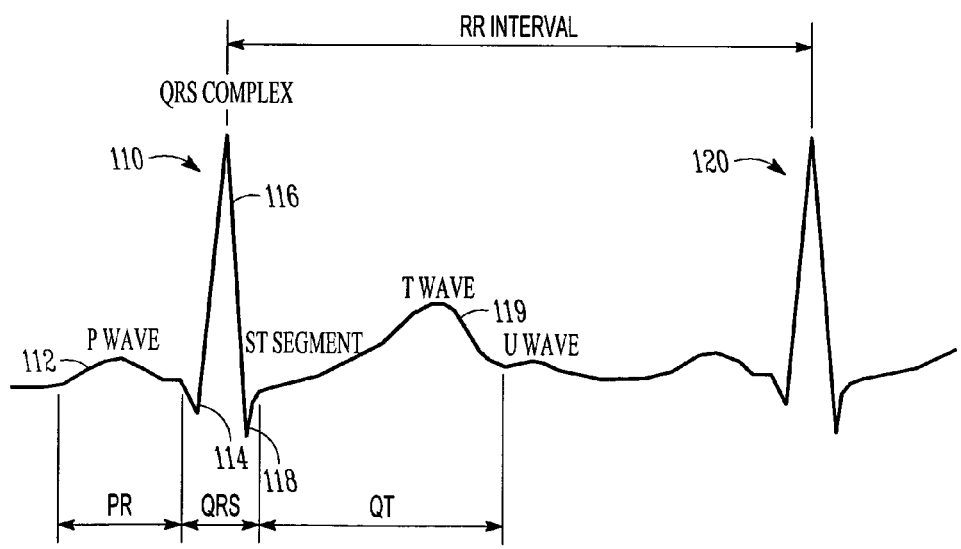

Referring to FIGS. 1A and 1B, an ECG waveform 100 describes the activation sequence of a patient's heart as recorded, for example, by a bipolar cardiac sensing electrode. The graph of FIG. 1A illustrates an example of the ECG waveform 100 for three heartbeats, denoted as a first heartbeat 110, a second heartbeat 120, and a third heartbeat 130. FIG. 1B is a magnified view of the first two heartbeats 110, 120 of the ECG waveform identified by bracket 1B in FIG. 1A.

Referring to the first heartbeat 110, the portion of the ECG waveform representing depolarization of the atrial muscle fibers is referred to as a P-wave 112. Depolarization of the ventricular muscle fibers is collectively represented by a Q 114, R 116, and S 118 waves of the ECG waveform 100, typically referred to as the QRS complex, which is a well-known morphologic feature of electrocardiograms. Finally, the portion of the waveform representing repolarization of the ventricular muscle fibers is known as a T wave 119. Between contractions, the ECG waveform returns to an isopotential level. The segment of the cardiac cycle that includes the P-wave and extends to the S-wave is sometimes referred to as the P-QRS segment, and the segment that begins at the onset of the S-wave and includes the T-wave is referred to as the ST-T segment.

The sensed ECG waveform 100 illustrated in FIGS. 1A and 1B is typical of a far-field ECG signal, effectively a superposition of all the depolarizations occurring within the heart that result in contraction. The ECG waveform 100 may also be obtained indirectly, such as by using a signal separation methodology. Signal separation methodologies, such as blind source separation (BSS), are able to separate signals from individual sources that are mixed together into a composite signal. Signal separation works on the premise that spatially distributed electrodes collect components of a signal from a common origin (e.g., the heart) with the result that these components may be strongly correlated to each other. In addition, these components may also be weakly correlated to components of another origin (e.g., noise). A signal separation algorithm may be implemented to separate these components according to their sources and to produce one or more cardiac signal vectors associated with all or a portion of one or more cardiac activation sequences based on the source separation.

Figure 2:
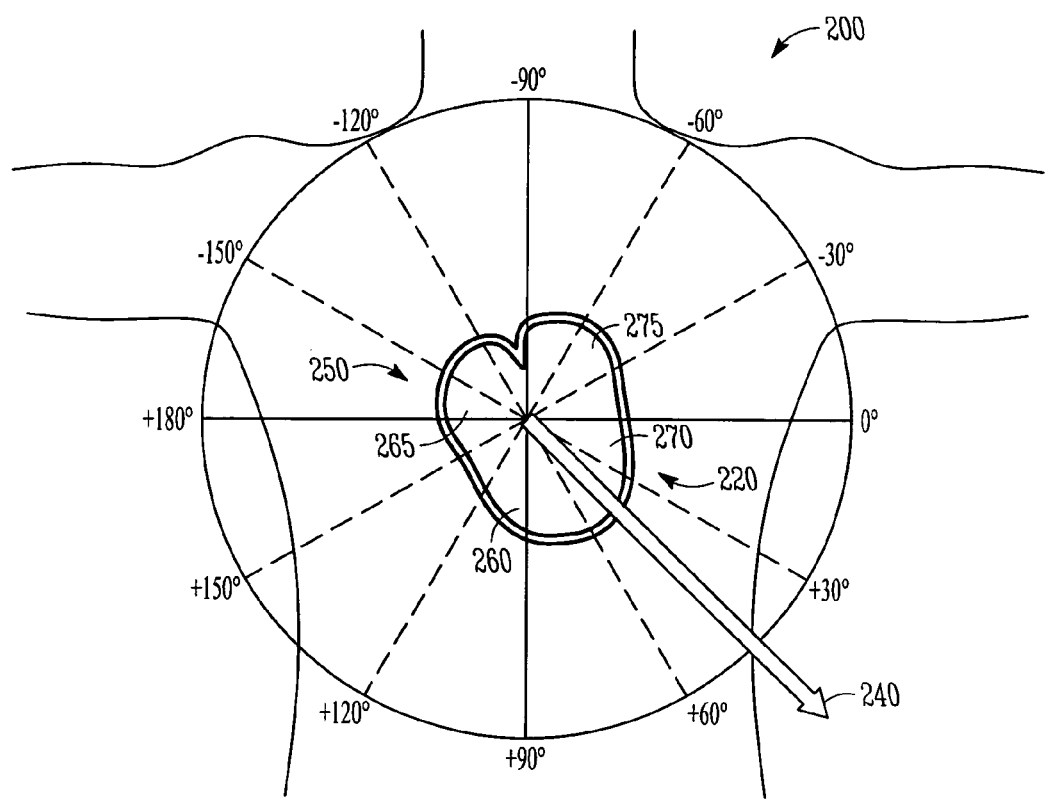
FIG. 2 illustrates referencing used to describe cardiac signal vectors associated with a depolarization wavefront.

FIG. 2 illustrates a convenient reference for describing cardiac signal vectors associated with a depolarization wavefront. FIG. 2 is a polar plot 200 of a cardiac vector 240 superimposed over a frontal view of a thorax 220, with the origin of the polar plot located at a patient's heart 250, specifically, the atrioventricular (AV) node of the heart 250. The heart 250 is a four-chambered pump that is largely composed of a special type of striated muscle, called myocardium. Two major pumps operate in the heart, and they are a right ventricle 260, which pumps blood into pulmonary circulation, and a left ventricle 270, which pumps blood into the systemic circulation. Each of these pumps is connected to its associated atrium, called a right atrium 265 and a left atrium 275.

The cardiac vector 240 is describable as having an angle, in degrees, about a circle of the polar plot 200, and having a magnitude, illustrated as a distance from the origin of the tip of the cardiac vector 240. The polar plot 200 is divided into halves by a horizontal line indicating 0 degrees on the patient's left, and +/−180 degrees on the patient's right, and further divided into quadrants by a vertical line indicated by −90 degrees at the patient's head and +90 degrees on the bottom. The cardiac vector 240 is projectable onto the two-dimensional plane designated by the polar plot 200.

The cardiac vector 240 is a measure of all or a portion of the projection of a heart's activation sequence onto the polar plot 200. The heart possesses a specialized conduction system that ensures, under normal conditions, that the overall timing of ventricular and atrial pumping produces adequate cardiac output, the amount of blood pumped by the heart per minute. As described earlier, the normal intrinsic pacemaker of the heart is a self-firing unit located in the right atrium called the sinoatrial node. The electrical depolarization generated by this structure activates contraction of the two atria. The depolarization wavefront then reaches the specialized conduction system using conducting pathways within and between the atria. The depolarization is conducted to the atrioventricular node, and transmitted down a rapid conduction system composed of the right and left bundle branches, to stimulate contraction of the two ventricles.

The normal pacemaker and rapid conduction system are influenced by intrinsic autonomic activity and by the autonomic nervous system, which modulates heart rate and the speed with which electrical depolarizations are conducted through the specialized conduction system. There are many diseases that interfere with the specialized conduction system of the heart, and many result in abnormally fast, slow, or irregular heart rhythms.

Figure 3A:
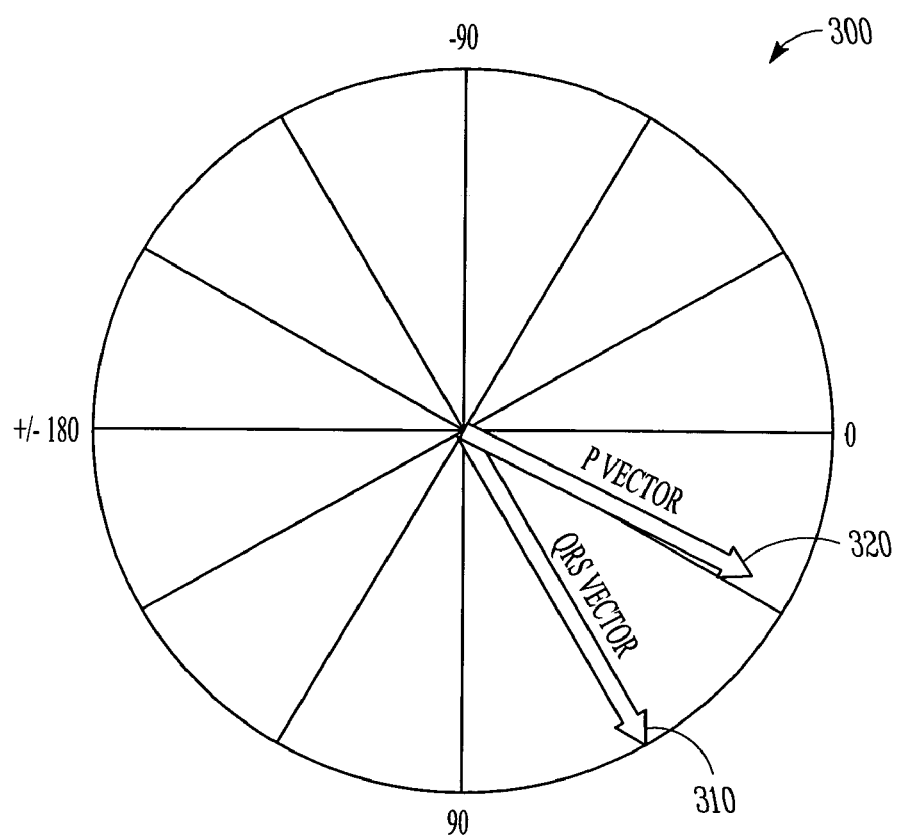
FIG. 3A illustrates a polar plot of separate portions of a cardiac cycle that may make up the cardiac vector.

The cardiac vector 240 may be, for example, associated with the entire cardiac cycle, and may describe the mean magnitude and mean angle of the cardiac cycle. Referring now to FIG. 3A, a polar plot 300 is illustrated of separate portions of the cardiac cycle that may make up the cardiac vector 240 of FIG. 2. As is illustrated in FIG. 3A, a QRS vector 310 and a P vector 320 are illustrated having approximately 60 degree and 30 degree angles, respectively. The QRS vector 310 may also be referred to as the QRS axis, and changes in the direction of the QRS vector may be referred to as QRS axis deviations.

The QRS vector 310 represents the projection of the mean magnitude and angle of the depolarization wavefront during the QRS portion of the cardiac cycle onto the polar plot 300. The P vector 320 represents the projection of the mean magnitude and angle of the depolarization wavefront during the P portion of the cardiac cycle onto the polar plot 300. The projection of any portion of the depolarization wavefront may be represented as a vector on the polar plot 300.

Further, any number of cardiac cycles may be combined to provide a statistical sample that may be represented by a vector as a projection onto the polar plot 300. Likewise, portions of the cardiac cycle over multiple cardiac cycles may also be combined, such as combining a weighted summation of only the P portion of the cardiac cycle over multiple cardiac cycles, for example.

Referring now to FIGS. 1A through 3A, the first, second, and third cardiac cycles 110, 120, and 130 may be analyzed using a window 140 (FIG. 1A) applied concurrently to signals sensed by three or more cardiac sense electrodes. The ECG waveform signals 100 from all the sense electrodes, during the window 140, may be provided to a signal processor. The signal processor may then perform a source separation that provides the cardiac vector 240 (FIG. 2). The cardiac vector 240 then represents the orientation and magnitude of the cardiac vector that is effectively an average over all three cardiac cycles 110, 120, and 130.

Other windows are also useful. For example, a window 150 and a window 160 may each provide a full cardiac cycle, such as the cardiac cycle 120 and the cardiac cycle 130 illustrated in FIG. 1A, to a controller or processor for analysis. The windows 150, 160 may be useful for beat-to-beat analysis, where the angle, magnitude, or other useful parameter from the separated cardiac vector 240 is compared between consecutive beats, or trended, for example.

Examples of other useful windows include a P-window 152, a QRS window 154, and an ST window 155 (FIG. 1A) that provide within-beat vector analysis capability, such as by providing the P-vector 320 and the QRS-vector 310 illustrated in FIG. 3A. Providing a P-window 162 and/or a QRS-window 164, and/or an ST window 165 to subsequent beats, such as to the consecutive cardiac cycle 130 illustrated in FIG. 1, provides for subsequent separations that may provide information for tracking and monitoring changes and/or trends of windowed portions of the cardiac cycle or statistical samples of P, QRS, or T waves over more than 1 beat.

Figure 3B:
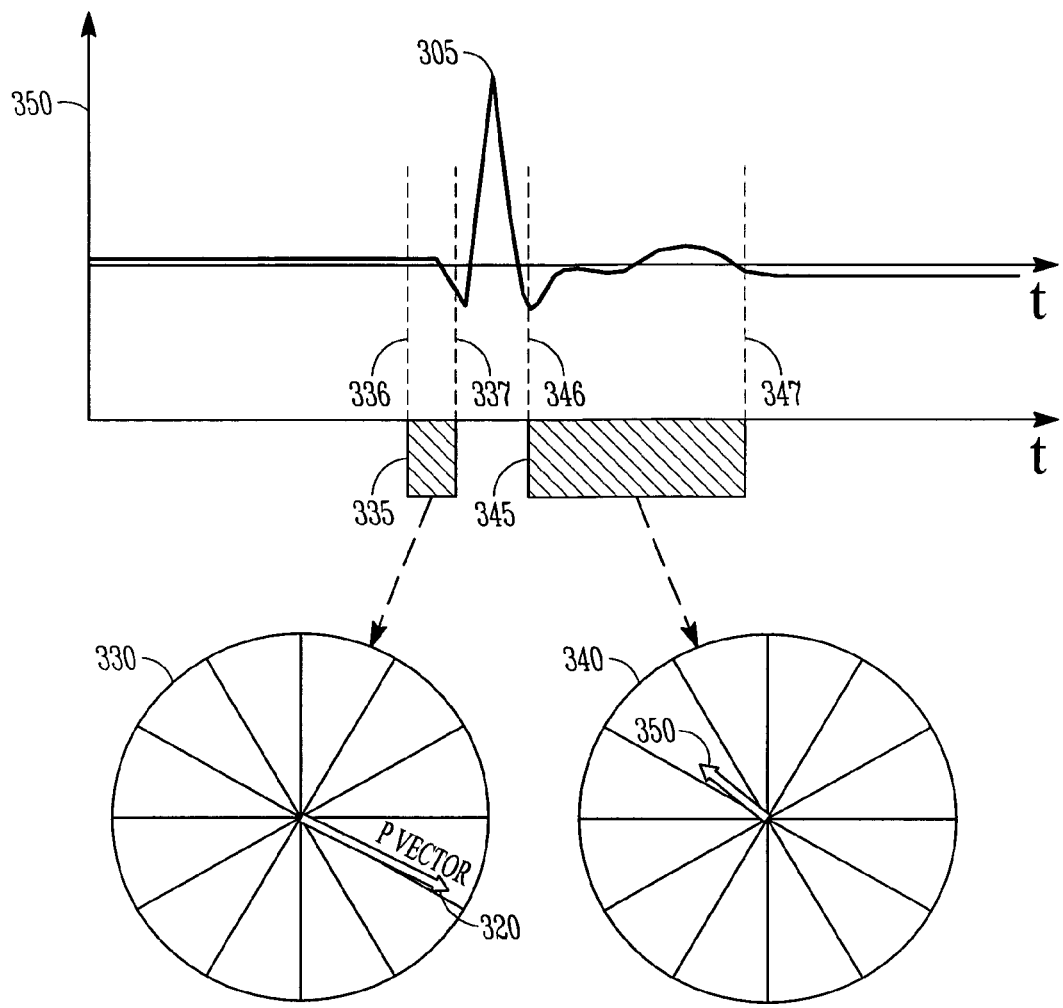
FIG. 3B illustrates polar plots of cardiac vectors obtained from selected portions of an electrocardiogram.

Referring now to FIG. 3B, polar plots of cardiac vectors obtained from selected portions of an electrocardiogram are illustrated. In general, it may be desirable to define one or more detection windows associated with particular segments of a given patient's cardiac cycle. The detection windows may be associated with cardiac signal features, such as P, QRS, ST, and T wave features, for example. The detection windows may also be associated with other portions of the cardiac cycle that change in character as a result of changes in the pathology of a patient's heart. Such detection windows may be defined as fixed or triggerable windows.

Detection windows may include unit step functions to initiate and terminate the window, or may be tapered or otherwise initiate and terminate using smoothing functions such as Bartlett, Bessel, Butterworth, Hanning, Hamming, Chebyshev, Welch, or other functions and/or filters. The detection windows associated with particular cardiac signal features or segments may have widths sufficient to sense cardiac vectors resulting from normal or expected cardiac activity. Aberrant or unexpected cardiac activity may result in the failure of a given cardiac vector to fall within a range indicative of normal cardiac behavior. Detection of a given cardiac vector beyond a normal range may trigger one or more operations, including increased monitoring or diagnostic operations, therapy delivery, patient or physician alerting, communication of warning and/or device/physiological data to an external system (e.g., advanced patient management system) or other responsive operation.

An ECG signal 305 is plotted in FIG. 3B as signal amplitude 350 on the ordinate versus time on the abscissa. One cardiac cycle is illustrated. The P portion of the ECG signal 305 may be defined using a P-window 335 that opens at a time 336 and closes at a time 337. A source separation performed on the ECG signal 305 within the P-window 335 produces the P vector 320 illustrated on a polar plot 330. The angle of the P vector 320 indicates the angle of the vector summation of the depolarization wavefront during the time of the P-window 335 for the ECG signal 305.

The ST portion of the ECG signal 305 may be defined using an ST-window 345 that opens at a time 346 and closes at a time 347. A source separation performed on the ECG signal 305 within the ST-window 345 produces the ST vector 350 illustrated on a polar plot 340. The angle of the ST vector 350 indicates the angle of the vector summation of the repolarization wavefront during the time of the ST-window 345 for the ECG signal 305.

The P vector 320 and the ST vector 350 may be acquired as baselines, for future comparisons. If baselines for the P vector 320 and the ST vector 350 are already established, the P vector 320 and ST vector 350 may be compared relative to their baselines for monitoring and tracking purposes. As indicated above, detection of P vector 320 or ST vector 350 beyond a predetermined range may trigger one or more responsive operations.

Cardiac activation sequence monitoring and tracking, to monitor changes and/or trends as described above, may be useful to determine initial activation sequences, and track acute and chronic changes in the activation sequences. Information from the patient's activation sequence is valuable for identification, discrimination, and trending of conditions such as conduction anomalies (e.g. AV block, bundle branch block, retrograde conduction) and cardiac arrhythmias (e.g. discriminating between supraventricular tachycardia versus ventricular tachycardia, reentrant supraventricular tachycardia versus atrial fibrillation, or other desirable discrimination.) In addition to baseline establishment, monitoring, and tracking, activation sequence information may also be useful for determining pace capture for autocapture/autothreshold algorithms, adjustment, optimization, or initiation of cardiac resynchronization therapy, and optimization or initiation of anti-arrhythmia therapies, for example.

Figure 4:
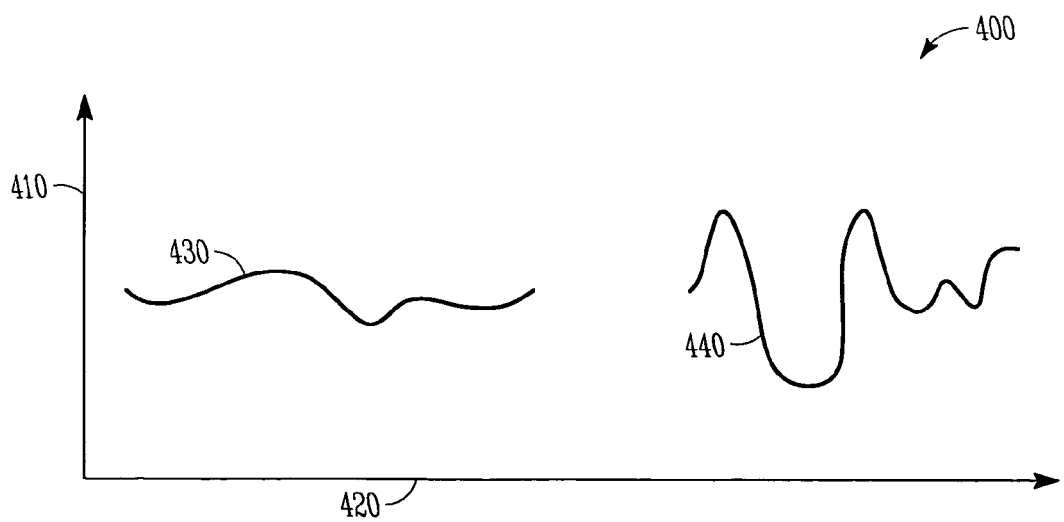
FIG. 4 is a graph of temporal profiles of a measure of a cardiac vector.

FIG. 4 illustrates another convenient reference for describing cardiac signal vectors associated with a depolarization wavefront. FIG. 4 is a graph 400 of temporal profiles of a measure of a cardiac vector useful for diagnosing diseases and anomalous conditions in accordance with the system and methods described. The graph 400 contains a first temporal profile 430 of a cardiac vector, and a second temporal profile 440 of the same cardiac vector after a change has occurred. An abscissa 420 of the graph 400 is time related, and an ordinate 410 of the graph 400 is related to a measure of the cardiac vector.

The ordinate 410 may be, for example, the angle of the cardiac vector. A non-limiting, non-exhaustive list of measures of a vector useful for the ordinate 410 includes: angle; magnitude; variance; power spectral density; rate of change of angle; rate of change of magnitude; rate of change of variance; or other measure indicative of a change in the cardiac activation sequence. As an example, consider the angle of the P vector 320 illustrated in FIG. 3A. In this example, the ordinate 410 would be indicated in degrees, with the first temporal profile 430 varying from around 30 degrees. The abscissa 420 may be time, designated in cardiac cycles, with a measure made of the P vector 320 for every cardiac cycle. The angle of the P vector 320 may be plotted on the graph 400 at any interval of cardiac cycles, thereby displaying variance and trends in the angle of the P vector 320 over many cardiac cycles.

Figure 5A:
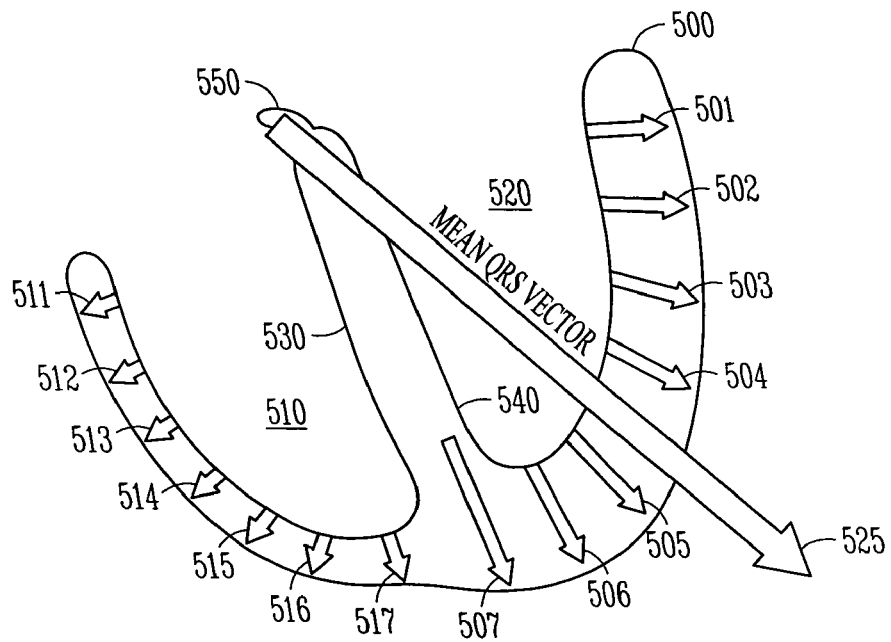
FIGS. 5A through 5D illustrate cardiac vectors superimposed over a sectional view of the ventricles of a patient's heart.

After some change occurs, such as a pathological change in the patient's heart, the second temporal profile 440 may be plotted using cardiac cycles occurring after the change. As is evident in the second temporal profile 440 versus the first temporal profile 430, the variance of the second temporal profile 440 is significantly larger than the variance of the first temporal profile 430. Changes such as this may be detected and used to diagnose, verify and/or monitor diseases and/or cardiac conditions. FIGS. 5A through 5D illustrate cardiac vectors superimposed over a sectional view of the ventricles of a patient's heart 500. Referring to FIG. 5A, the ventricular portion of a patient's heart is illustrated having a right ventricle 510 and a left ventricle 520 separated by the heart's septum. The specialized conduction system includes an atrioventricular node 550, which is used as the origin for cardiac vectors, such as a mean QRS vector 525.

A right bundle branch 530 conducts the depolarization wavefront from the atrioventricular node 550 to the wall of the right ventricle 510. Illustrated in the wall of the right ventricle 510 are a series of vectors 511-517, indicating the magnitude and angle of a local portion of the depolarization wavefront as it travels along the right ventricle 510.

A left bundle branch 540 conducts the depolarization wavefront from the atrioventricular node 550 to the wall of the left ventricle 520. Illustrated in the wall of the left ventricle 510 are a series of vectors 501-507, indicating the magnitude and angle of a local portion of the depolarization wavefront as it travels along the left ventricle 520.

The mean QRS vector 525 is the vector summation of the vectors 511-517 and the vectors 501-507. The mean QRS vector 525 may be typical of a healthy heart, here illustrated at about 40 degrees angle if using the polar plot of FIG. 3A. The mean QRS vector 525 varies from patient to patient depending on, for example, patient posture, and normal anatomical variation.

Figure 5B:
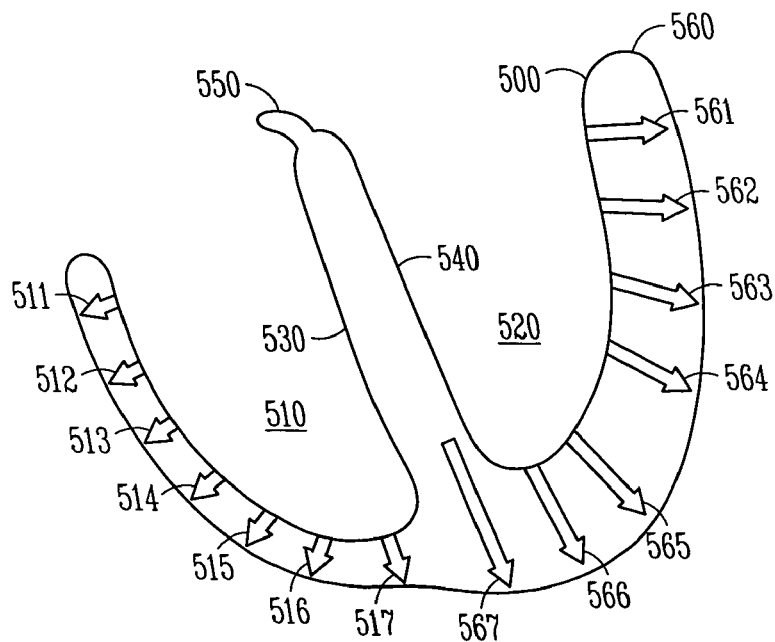

Referring now to FIG. 5B, the wall of the left ventricle 520 is enlarged, or hypertrophied, relative to FIG. 5A. In FIG. 5B, a dotted line 560 represents the wall of the left ventricle 520 in FIG. 5A, before hypertrophy. A series of local vectors 561-567 illustrate the larger local contribution to the mean QRS vector 525 from the hypertrophy related vectors 561-567 relative to the normal series of left ventricle vectors 501-507.

Figure 5C:
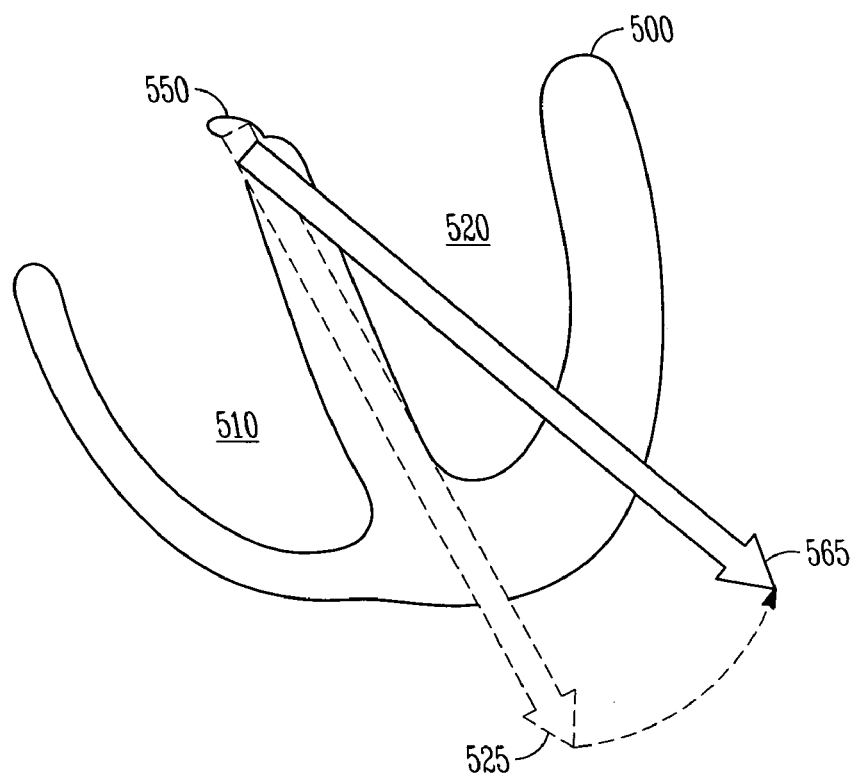

FIG. 5C illustrates how the mean QRS vector 525 from a normal heart may change to a mean hypertrophied QRS vector 565 after hypertrophy has occurred. For example, an IMD may be implanted in a patient, and an initial analysis provides a baseline mean QRS vector 525 for the patient, indicative of a normal condition of the left ventricle 520. After a period of time, the patient's heart may be subject to hypertrophy. An analysis performed post-hypertrophy may result in finding the mean hypertrophied QRS vector 565. This change may be used to diagnose, verify and/or monitor hypertrophy of the patient's left ventricle.

Figure 5D:
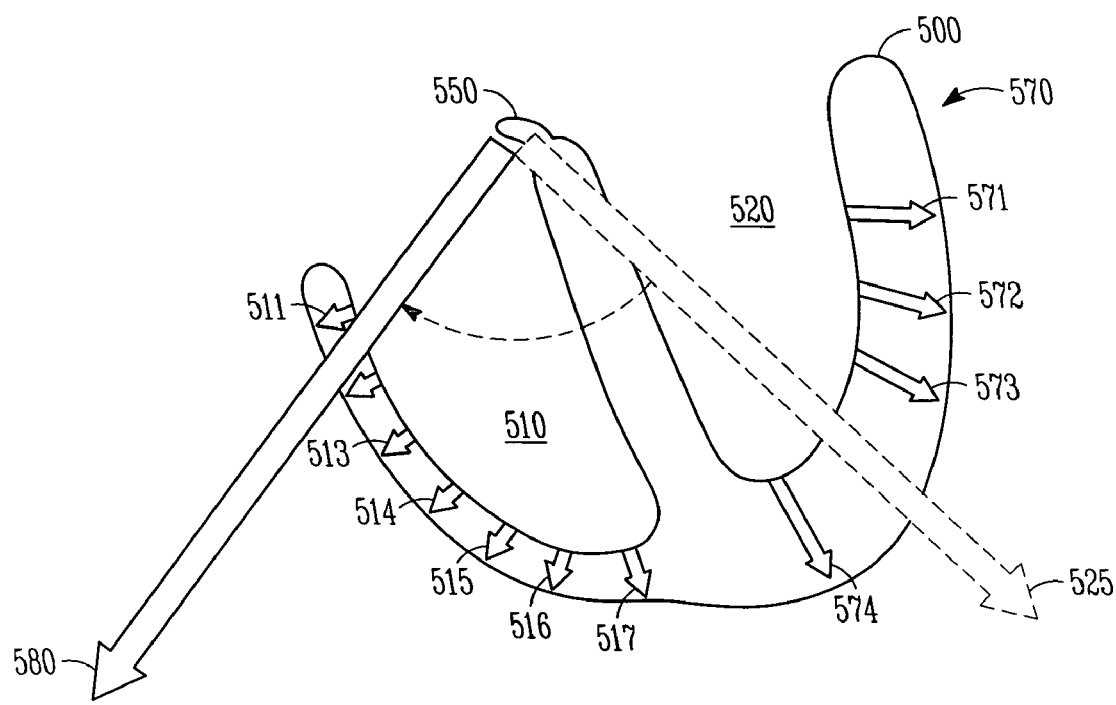

Another example of a pathological change that may be diagnosed and/or verified using source separation is myocardial infarction. The sectional view in FIG. 5D illustrates the left ventricle 520 having an infarcted portion 570 of the ventricular wall. The measurements were developed from a surface ECG. As is evident in the infarcted portion 570, no depolarization is occurring, so only local depolarization vectors 571-574 contribute to the mean cardiac vector from the left ventricle 520. The infarction results in a change, for example, of the detected mean QRS vector 525 to an infarcted mean QRS vector 580. Alternatively, the ST vector or the ST-T vector may show the change. This change is evident as the angle of the cardiac vector moves from the second quadrant before infarction, to the third quadrant after infarction. The location and extent of the infarction impacts the direction and magnitude of the shift in the vector or vectors.

Figure 5E:
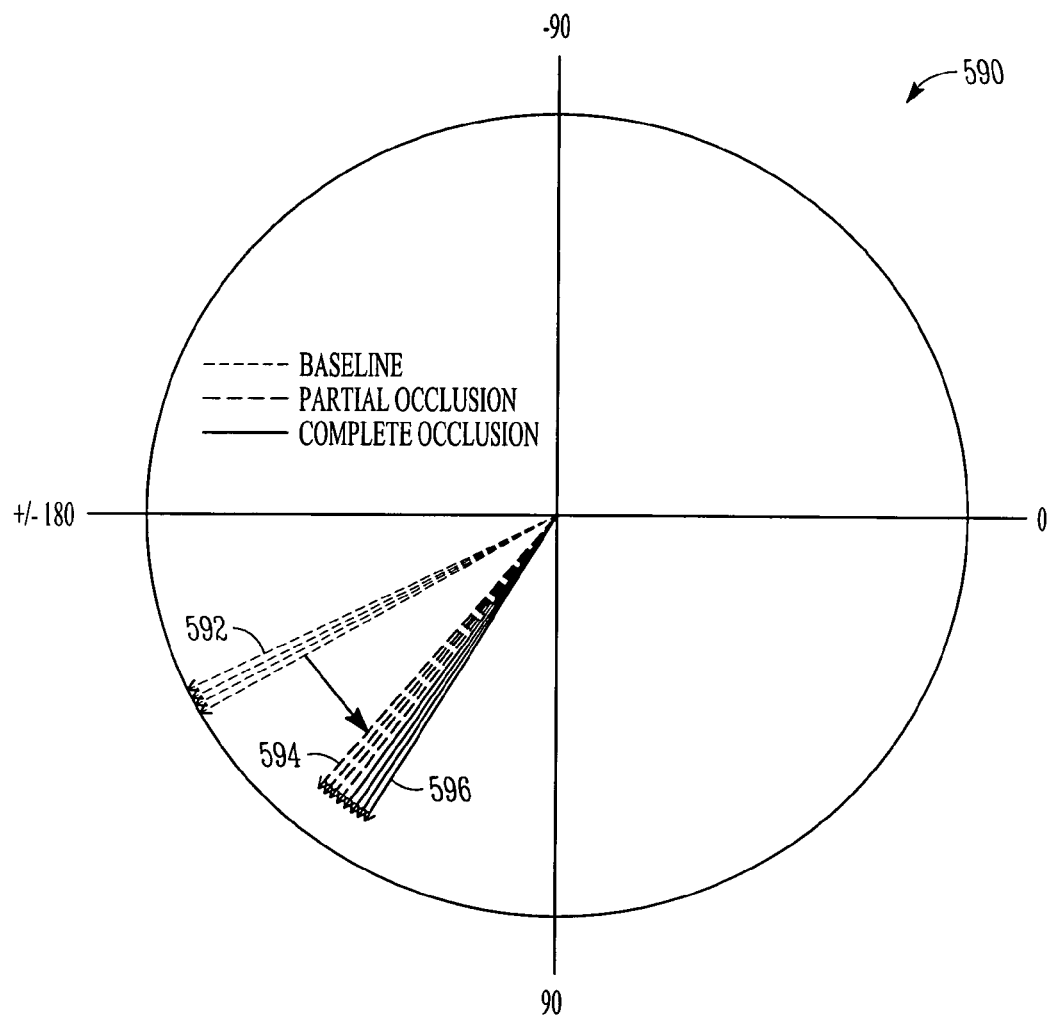
FIG. 5E is a graph illustrating activation sequence vector angles for an ST-T segment of a cardiac signal.

FIG. 5E is a graph 590 illustrating activation sequence ST-T vector angles for the ST-T segment of a cardiac signal. The measurements were developed from a live porcine subject using a wireless ECG system. A dominant vector of multiple individual activation sequence vectors is computed from multiple subcutaneous ECGs when monitoring and/or tracking cardiac activation sequence information. A baseline vector 592 for the dominant ST-T vector is shown. The graph 590 shows a shift in the dominant vector of ST-T vectors from the baseline vector 592 at approximately 155 degrees to a dominant vector corresponding to partial occlusion of the left anterior descending coronary artery 594 at about 125 degrees, and to a dominant vector corresponding to complete occlusion of the left anterior descending coronary artery 596. An IMD that detects a change such as is illustrated in FIG. 5E has the potential to alert the patient and/or physician to a loss or lessening of blood supply to a portion of the heart muscle before permanent damage occurs. Such early ischemia detection may result in greatly reduced morbidity from these kinds of events.

Figure 6A:
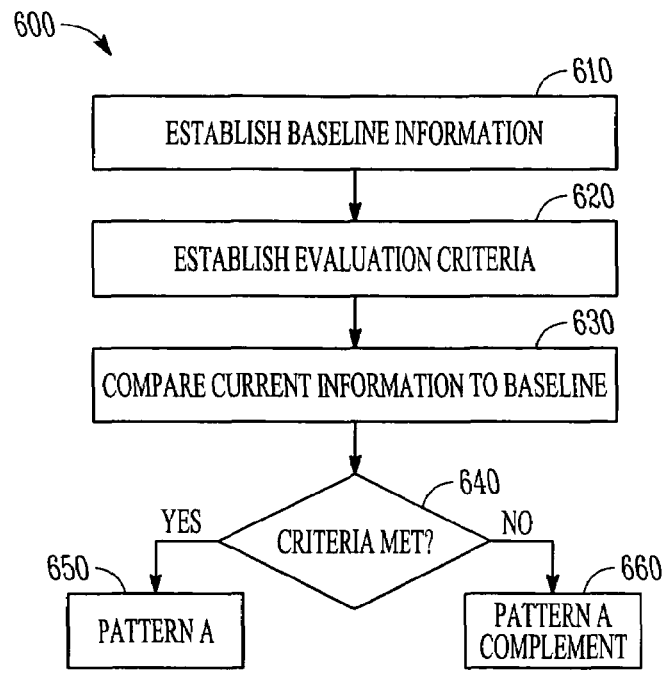
FIGS. 6A and 6B are block diagrams of a method of detecting a change in one or more cardiac signal vectors associated with all or a portion of one or more cardiac activation sequences based on a source separation.

FIG. 6A is a block diagram of a method 600 of detecting a change in one or more cardiac signal vectors associated with all or a portion of one or more cardiac activation sequences based on a source separation. A baseline is established 610, providing information that may be monitored or tracked relative to a patient's electrophysiological signals. The baseline 610 may be established from an initial source separation that provides initial cardiac signal information as a baseline. Alternately, or additionally, the baseline 610 may be established by an IMD manufacturer from clinical data, or a patient's baseline 610 may be established by a clinician before, during, or after an IMD implant procedure. The baseline 610 may be established as a rolling average of recent patient information from prior source separations, for example.

Evaluation criteria are established 620 to provide an index for comparison to the baseline 610. For example, the evaluation criteria 620 may be any parameter or characteristic determinable or measurable from the patient's electrophysiology information. A non-exhaustive, non-limiting list of evaluation criteria 620 includes: an angle change of one or more cardiac signal vectors; a magnitude change of one or more cardiac signal vectors; a variance change of one or more cardiac signal vectors; a power spectral density change of the angle of one or more cardiac signal vectors; a power spectral density change of the magnitude of one or more cardiac signal vectors; a trajectory change of one or more cardiac signal vectors; a temporal profile change of one or more cardiac signal vectors; a rate of change of angle of one or more cardiac signal vectors; a rate of change of magnitude of one or more cardiac signal vectors; a rate of change of variance of one or more cardiac signal vectors; a rate of change of temporal profile of one or more cardiac signal vectors; a trend of the angle of one or more cardiac signal vectors; a trend of the magnitude of one or more cardiac signal vectors; a trend of the variance of one or more cardiac signal vectors; and a trend of the temporal profile of one or more cardiac signal vectors.

For example, an initial source separation may be performed by an IMD on a patient post-implant. The separation may produce the baseline 610 of the patient's average full cardiac cycle, such as the cardiac vector 240 illustrated in FIG. 2. The vector 240 may have a characteristic, such as the angle, determined as +45 degrees. The evaluation criteria 620 may be, for example, that the patient's average full cardiac cycle vector's angle should be within +40 to +50 degrees.

A comparison 630 is performed to determine the latest patient information relative to the baseline 610. For example, the results of a latest source separation algorithm may provide the latest average full cardiac cycle vector's angle for the patient. Continuing with the above example, the comparison 630 may check the latest angle of the patient's average full cardiac cycle vector's angle against the +40 to +50 degree criteria.

A decision 640 selects an outcome based on the comparison 630. If the criteria is met, for example if the latest angle is within +40 to +50 degrees as outlined above, then a pattern A 650 is considered to be the patient's latest condition. For example, the pattern A 650 may be defined as an insufficient change to require some sort of action by the IND. If a criterion 620 is not met at decision 640, then a pattern A complement 660 condition is considered to be the patient's latest condition. The pattern A complement 660 condition may be defined as requiring some sort of action by the IMD, such as reporting the condition, further evaluating the patient's cardiac rhythms, preparing a defibrillator for a shock, or other desired action.

Figure 6B:
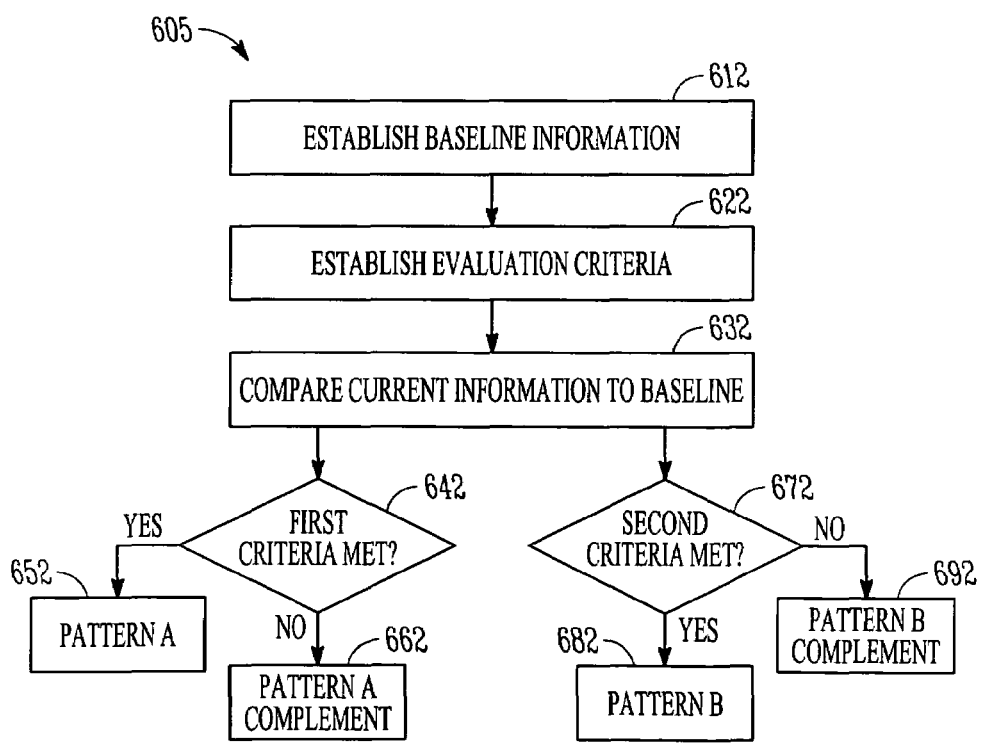

FIG. 6B is a block diagram of another embodiment of a method 605 of detecting a change in one or more cardiac signal vectors associated with all or a portion of one or more cardiac activation sequences, when the criteria for baseline shift includes two criteria. It is contemplated that any number of criteria may be used or combined in the systems and methods described. The use of two criteria with reference to FIG. 6B is for purposes of explanation as to how to extend the methods to multiple criteria, and is not intended as a limiting example.

A baseline is established 612, providing information that may be monitored or tracked from a patient's electrophysiological signals. The baseline 612 may be established from an initial source separation that provides initial cardiac signal information as a baseline. Alternately, or additionally, the baseline 612 may be established by an IMD manufacturer from clinical data, or a patient's baseline 612 may be established by a clinician before, during, or after an IMD implant procedure. The baseline 612 may be established as a rolling average of recent patient information from prior source separations, for example.

Evaluation criteria are established 622 to provide indices for comparison to the baseline 612. For example, the evaluation criteria 622 may be any parameters or characteristics determinable or measurable from the patient's electrophysiology information. A non-exhaustive, non-limiting list of evaluation criteria 622 includes those described previously with respect to FIG. 6A. It is further contemplated that a single criterion may be compared with respect to multiple baselines, and/or that multiple criteria may each be compared with respect to their own unique baseline established for each particular criterion.

Baselines may be pre-defined using, for example, clinical data, and/or baselines may be established using initial source separations. For example, and described in more detail below, a source separation may provide an orthogonal coordinate system; with vectors described using a series of coefficients matched to a series of unit direction vectors. One or more angles may be calculated using trigonometric identities to indicate a vector's direction relative to other vectors in the coordinate system. Subsequent source separations provide revised sets of coefficients, from which changes in vector direction may be determined using the same trigonometric identities. In an n-dimensional space, (n−1) angles may be resolved and used for comparison and tracking.

For example, an initial source separation may be performed by an IMD on a patient post-implant. The separation may produce the baseline 612 of the patient's cardiac cycle, such as the QRS-vector 310 and the P-vector 320 illustrated in FIG. 3A. The QRS-vector 310 may have the angle determined as +45 degrees. The P-vector 320 may have the angle determined as +28 degrees. The evaluation criteria 622 may be, for example, that the patient's QRS-vector's angle should be within +40 to +50 degrees and that the patient's P-vector angle should be within +25 to +30 degrees.

A comparison 632 is performed to determine the latest patient information relative to the baseline 612. For example, the results of a latest source separation algorithm may provide the latest angles of the QRS-vector and P-vector for the patient. Continuing with the above example, the comparison 632 may check the latest angles of the patient's QRS-vector and P-vector against the +40 to +50 degree and +25 to +30 degree criteria respectively.

A first decision 642 selects a first outcome based on the comparison 632. If the first criteria is met, for example if the latest angle of the QRS-vector is within +40 to +50 degrees as outlined above, then a pattern A 652 is considered to be the patient's latest condition. For example, the pattern A 652 may be defined as an insufficient change to require some sort of action by the IMD. If a criterion 622 is not met at decision 642, then a pattern A complement 662 condition is considered to be the patient's latest condition. The pattern A complement 662 condition may be defined as requiring some sort of action by the IMD, such as reporting the condition, further evaluating the patient's cardiac rhythms, preparing a defibrillator for a shock, or other desired action.

A second criteria decision 672 is performed to check for a second outcome based on the second criteria. If the second criteria is met, for example if the latest angle of the P-vector is within +25 to +30 degrees as outlined above, then a pattern B 682 is considered to be the patient's latest condition. For example, the pattern B 682 may be defined as an insufficient change to require some sort of second action by the IMD. If the criterion 622 is not met at decision 672, then a pattern B complement 692 condition is considered to be the patient's latest condition. The pattern B complement 692 condition may be defined as requiring some sort of second action by the IND.

Table 1 below provides a non-limiting non-exhaustive list of conditions that may be detected by monitoring and/or tracking cardiac activation sequences in the systems and methods described.

TABLE 1

Conditions associated with QRS Axis Deviations

First Source (Normal −30 to +90 degrees)

Left Axis Deviation: ≧−30°

Left Anterior Fascicular Block (LAFB) axis −45° to −90°
Some cases of inferior myocardial infarction
with QR complex
Inferior Myocardial Infarction +
LAFB in same patient (QS or QRS complex)
Some cases of left ventricular hypertrophy
Some cases of left bundle branch block
Ostium primum Atrial Septal Defect and other endocardial cushion defects
Some cases of Wolff-Parkinson-White syndrome syndrome
(large negative delta wave)
Right Axis Deviation: ≧+90°

Left Posterior Fascicular Block (LPFB):
Many causes of right heart overload and pulmonary hypertension
High lateral wall Myocardial Infarction
with QR or QS complex
Some cases of right bundle branch block
Some cases of Wolff-Parkinson-White syndrome
Children, teenagers, and some young adults
Bizarre QRS axis: +150° to −90°

Figure 7:
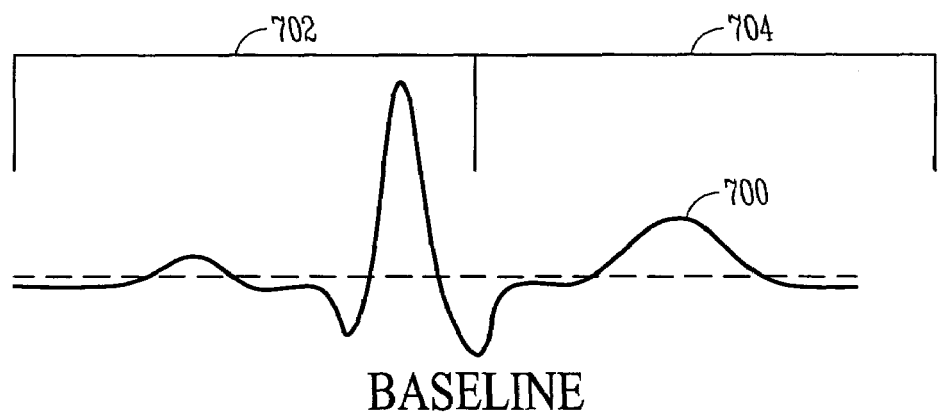
FIG. 7 illustrates ECG signal waveforms.
Figure 7:
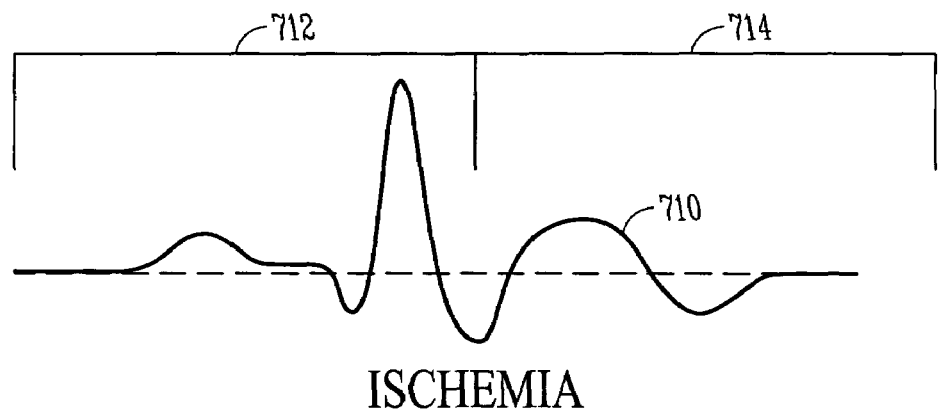

Dextrocardia
Some cases of complex congenital heart disease (e.g., transposition)
Some cases of ventricular tachycardia Second Source QRS Axis Deviation Left anterior fascicular block (LAFB)
Right ventricular hypertrophy
Left bundle branch block Acute Myocardial Infarction:
Hypertensive heart disease
Coronary artery disease
Idiopathic conducting system disease
Acute Myocardial Infarction -
inferior left ventricular free wall accessory pathway TABLE 1-continued Conditions associated with QRS Axis Deviations (Wolff-Parkinson-White syndrome)
Posteroseptal accessory pathway
left posterior fascicular block
Chronic Obstructive Pulmonary Disease (uncommon - 10%)
Other conduction defects:
left ventricular hypertrophy
Right bundle branch block
Elevated diaphragm: R anterior hemiblock
Pregnancy
Pacing of R ventricle
Abdominal mass
Pulmonary conditions
Ascites
Pulmonary hypertension
Tumor
Chronic Obstructive Pulmonary Disease
Conduction defects: Emphysema/bronchitis
R ventricular (apical) pacing
Pulmonary emboli/infarcts
Systemic hypertension, esp. chronic
Congenital defects
Valvular lesions
Rheumatic heart disease
Pulmonic stenosis
Aortic regurgitation
Mitral regurgitation
Mitral stenosis
Coarctation of the aorta
Tricuspid regurgitation
Hyperkalemia
Pulmonic stenosis
Normal variant in obese and in elderly
Pulmonic regurgitation As discussed previously in regard to FIG. 5E, monitoring the ST-T segment by source separation is useful in detecting occlusion. However, posture changes of the patient may also cause a deviation in the ST segment of an ECG signal. This could lead to the source separation measurement process providing false indications of ischemia. Posture changes affect the morphology of an ECG signal over the complete cardiac cycle while ischemia is most likely to mainly affect the ST-T wave. FIG. 7 illustrates a baseline ECG signal waveform 700 and an ECG signal waveform reflecting ischemia 710. The waveforms 700, 710 are separated into P-QRS segments 702, 712 and ST-T segments 704, 714. The change between the P-QRS segments 702, 712 is mostly due to any change in posture of the patient. The change between the ST-T segments 704, 714 includes both a change due to any posture change and the change due to ischemia.

Figure 8:
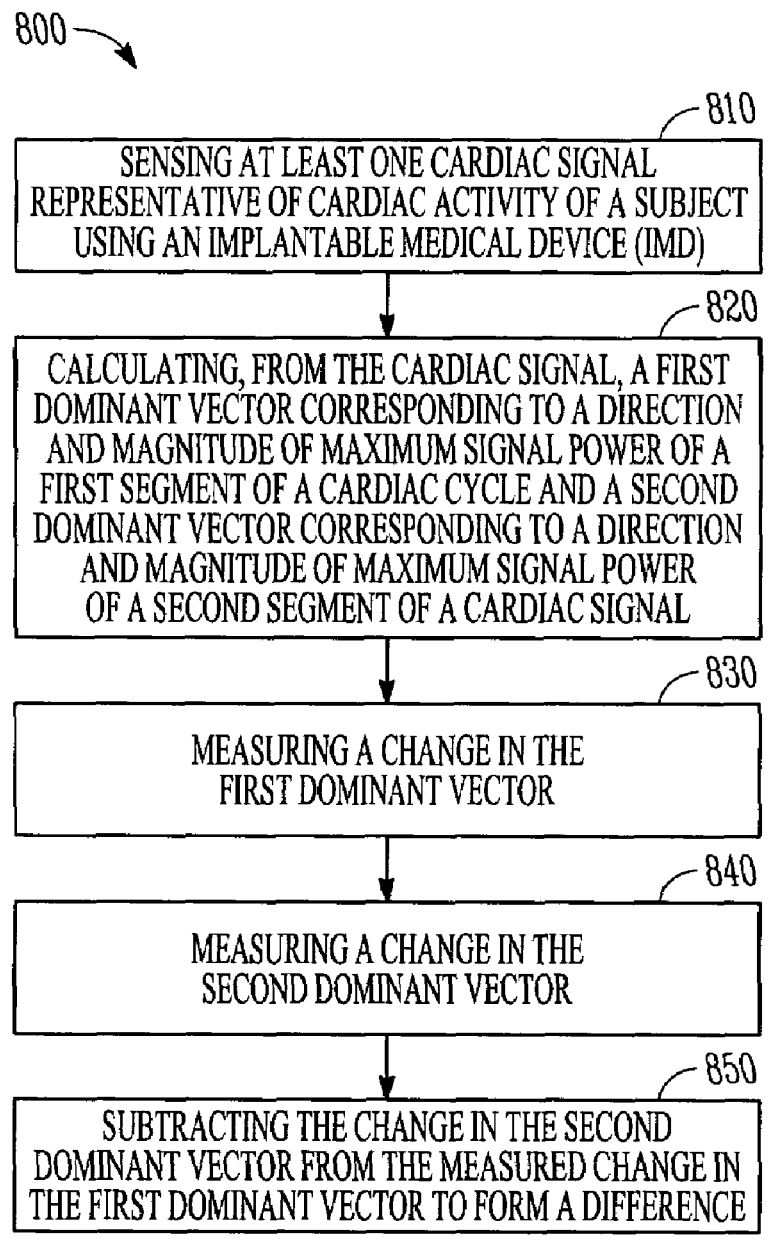
FIG. 8 is a block diagram of an example of a method of rejecting noise in cardiac activity measurements.

FIG. 8 is a block diagram of an example of a method 800 of rejecting noise in cardiac activity measurements. At 810, at least one cardiac signal representative of cardiac activity of a subject is sensed using an implantable medical device (IMD). At 820, a first dominant vector corresponding to a direction and magnitude of maximum signal power of a first segment of a cardiac cycle and a second dominant vector corresponding to a direction and magnitude of maximum signal power of a second segment of a cardiac cycle are calculated from the cardiac signal. A dominant vector is calculated from a central tendency of the vector, such as a mean magnitude and direction of the vector for example. In some examples, the first segment includes the ST-T segment and the second segment includes the P-QRS segment, but other segments or combination of segments can be used.

At 830, a change is measured in the first dominant vector. At 840, a change is measured in the second dominant vector. In some examples, measuring a change includes measuring a change in at least one of a change in the direction angle of a dominant vector and a change in the magnitude of a dominant vector. In some examples, measuring a change includes establishing a baseline vector, such as by computing a central tendency of a dominant vector, and measuring a change from the baseline. In some examples, measuring a change includes trending at least one dominant vector, and detecting a change from the trending. If the change in the first dominant vector includes a measured change that is of interest as well as measured noise, and the second dominant vector includes mostly measured noise, then the measured change of interest is obtained by (at 850) subtracting the change in the second dominant vector from the measured change in the first dominant signal vector to form a difference. The difference includes the measured change that is of interest with the noise reduced.

Figure 9:
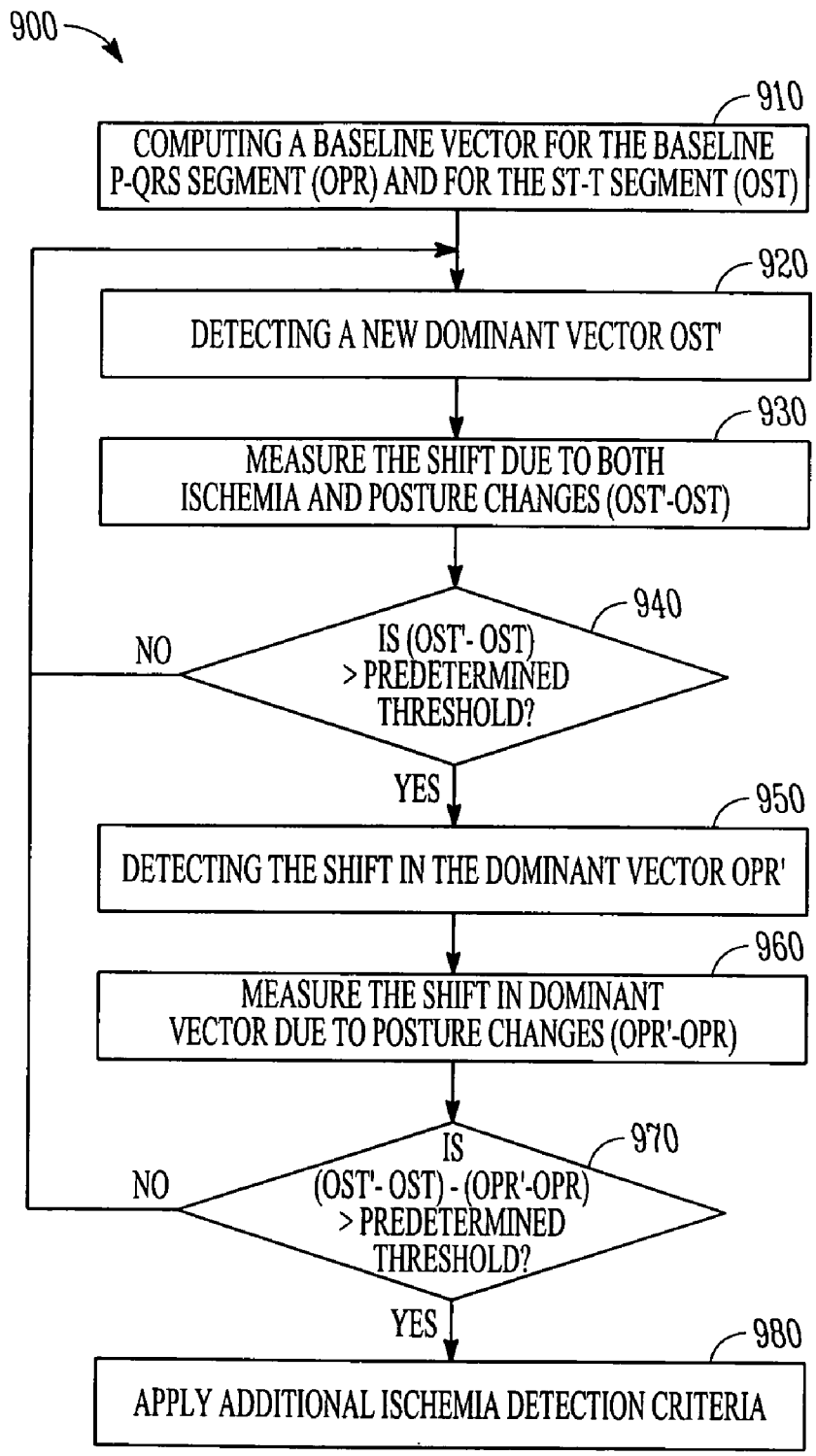
FIG. 9 shows a flow chart of an example implementation of a method to separate posture noise from an ischemia measurement.

As discussed previously, postures changes are a source of noise in ischemia measurements. FIG. 9 shows a flow chart of an example implementation of the more general method of FIG. 8 to separate posture noise from the ischemia measurement. Referring to FIGS. 9 and 7, at 910, a baseline vector is computed for the baseline P-QRS segment 702 ($O_{PR}$) and a baseline vector is computed for the baseline ST-T segment 712 ($O_{ST}$). When an ischemic event or episode occurs, a shift in the dominant vector of the P-QRS segment ($O_{PR}'$) occurs and a change in the dominant vector of the ST-T segment ($O_{ST}'$) occurs. At 920, the shift in the dominant vector $O_{ST}'$ is detected. The difference between the post-ischemia dominant vector of the ST-T vector and the baseline vector ($O_{ST}'-O_{ST}$) reflects a measured shift due to both ischemia and posture changes. This difference is measured at 930. At 940 it is determined whether the shift is greater than predetermined shift threshold. Predetermined refers to the threshold value being fixed or to the threshold value being programmable.

At 950, the shift in the dominant vector $O_{PR}'$ is determined. Because any measured shift in the P-QRS segment would be mostly due to any change in posture from the patient, the difference between the post-ischemia dominant vector of the P-QRS vector and the dominant baseline vector ($O_{PR}'-O_{PR}$) reflects a shift due to posture changes. At 960, this difference is measured. To obtain the measured shift due to ischemia without the posture change, the difference in the vectors of the P-QRS segment is subtracted from the difference in the vectors of the ST-T segments, i.e.

$$\text{Shift due to ischemia} = (O_{ST}'-O_{ST})-(O_{PR}'-O_{PR}). \quad (1)$$

At 970, the shift due to ischemia is compared to a predetermined threshold. The predetermined threshold in 970 may be the same threshold value as in 940 or it may be a different threshold value. If the shift due to ischemia is greater than a threshold shift, then an ischemic event may be declared, or preferably, the fact that such a shift occurred is combined with other ischemia detection criteria at 980.

In some examples, the measured shift in the ST segment is combined with the measured output from one or more sensors, such as to measure intracardiac or trans-thoracic impedance, blood pressure. In some examples, at least one rule is used to blend the outputs of the various sensors to make a decision as to whether a patient has experienced an ischemic event. In some examples, weights are assigned to corresponding outputs of the sensors and the ST measurement, and at least one rule is applied to merge the sensor outputs and the measured shift in the ST segment using the weights and determine whether an ischemic event occurred. In some examples, one or more fuzzy logic rules are applied that use the weights to merge the sensor outputs and the measured shift in the ST segment to determine whether an ischemic event occurred.

In some examples, an ischemic event is not declared unless the threshold is exceeded in X of Y consecutive cardiac cycles, where X is a positive integer less than positive integer Y. As an illustrative example, X is eight and Y is ten and an ischemic event is not declared unless the predetermined threshold is exceeded in at least eight of ten cardiac cycles.

Figure 10:
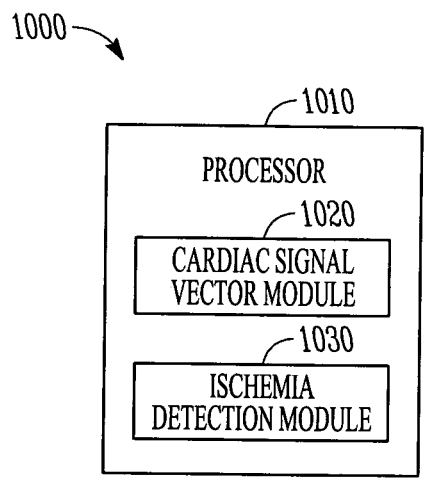
FIG. 10 is a block diagram of a system to implement a source signal separation measurement.

FIG. 10 is a block diagram of a system 1000 comprising a processor 1010 that includes a cardiac signal vector module 1020 and an ischemia detection module 1030. The cardiac signal vector module 1020 measures a first dominant vector corresponding to a direction and magnitude of maximum signal power of a first segment of at least one cardiac cycle of a subject and at least a second dominant vector corresponding to a direction and magnitude of maximum signal power of a second segment of the cardiac cycle from an electrical cardiac signal. The cardiac signal vector module 1020 measures a dominant vector by any of the methods described previously. The first and second segments can be any segments of the cardiac cycle such as the ST-T segment and the P-QRS segment.

The ischemia detection module 1030 measures a change in the first dominant vector. In some examples, the cardiac signal vector module 1020 computes a baseline vector for each of the dominant vectors and the ischemia detection module 1030 measures a change in the first and second dominant vector by measuring a change from the baselines. The ischemia detection module 1030 forms a difference by subtracting a measured change in the second dominant vector from the measurement of the change in the first dominant vector. Whether an ischemic event occurred is declared using the difference using any of the methods described previously.

In some examples, the processor 1010 is included in an implantable medical device (IMD). Examples of an IMD include, without limitation, a pacer, a defibrillator, a cardiac resynchronization therapy (CRT) device, or a combination of such devices. Other examples include implantable diagnostic devices, a drug pump, and a neural stimulation device.

Figure 11:
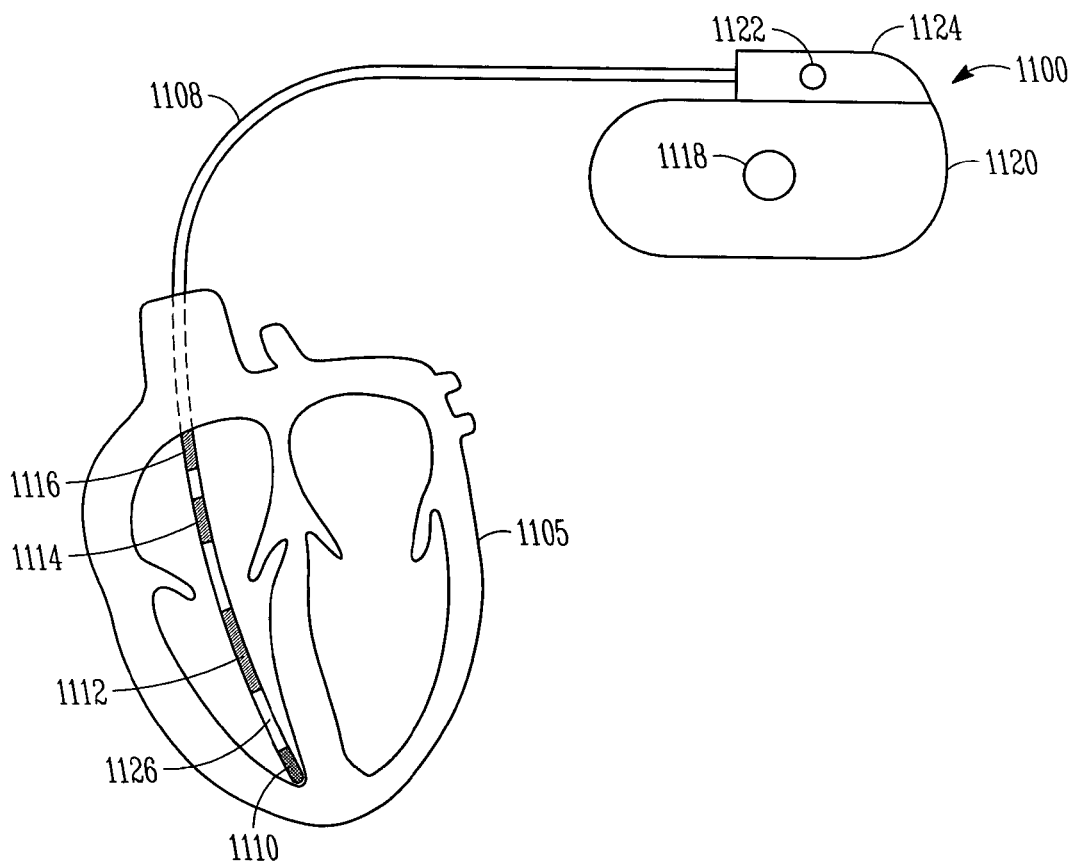
FIG. 11 is an illustration of portions of an IMD coupled by a lead or leads to a heart.

FIG. 11 is an illustration of portions of an IMD 1100 coupled by a lead 1108 or leads to a heart 1105. Lead 1108 includes one or more electrodes 1110, 1112, 1114, and 1116. The electrodes include an electrical connection to individual lead wires. The electrodes are separated by insulating segments 1126. In the lead example shown, tip electrode 1110 and ring electrode 1112 are for placement in the right ventricle, and ring electrodes 1114 and 1116 are for placement in the right atrium. The electrodes provide for sensing signals, delivering pacing therapy, or both sensing signals and delivering pacing therapy. Voltages are sensed differentially, such as between electrodes 1110 and 1112 in the ventricle and 1114 and 1116 in the atrium, or pacing energy is delivered differentially between the electrodes, or pacing and sensing are provided differentially. In some examples, the electrodes include an electrode 1118 formed on the IMD can 1120. In some examples, the entire can 1120 is an electrode. In some examples, the electrodes include an electrode 1122 formed on the IMD header 1124.

In some examples, electrodes 1110 and 1112 are provided on a first lead and electrode 1114 is a tip electrode and electrode 1116 is a ring electrode provided on a second lead. In some examples, an additional lead that includes ring electrodes placed in a coronary vein lying epicardially on the left ventricle via the coronary vein to provide sensing and or pacing to the left ventricle.

Lead 1108 optionally also delivers atrial cardioversion, atrial defibrillation, ventricular cardioversion, ventricular defibrillation, or combinations thereof to heart 1105 through the electrodes. Such electrodes typically have larger surface areas than pacing electrodes in order to handle the larger energies involved in defibrillation. A lead optionally provided in the left ventricle via the coronary vein provides resynchronization therapy to the heart 1105.

Figure 12A:
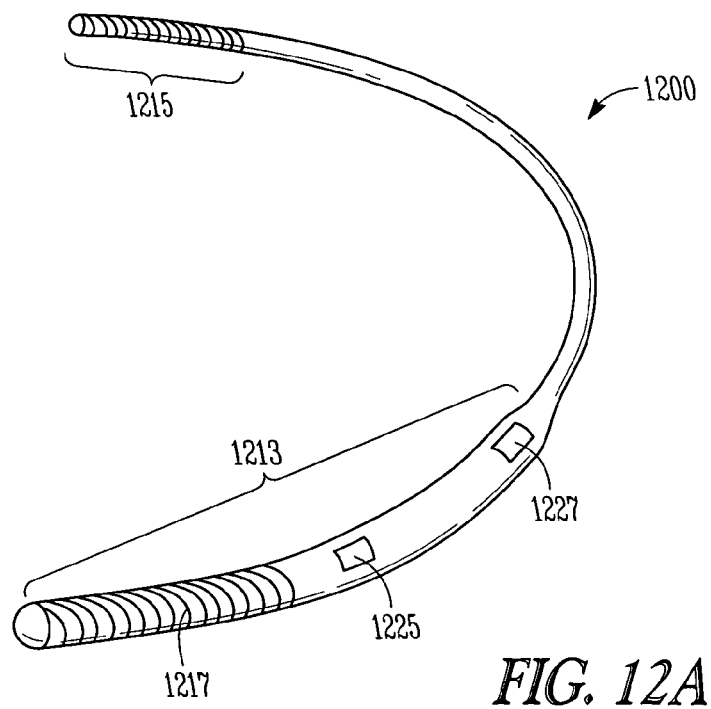
FIGS. 12A and 12B show an example of an IMD that does not use intravascular leads to sense cardiac signals.
Figure 12B:
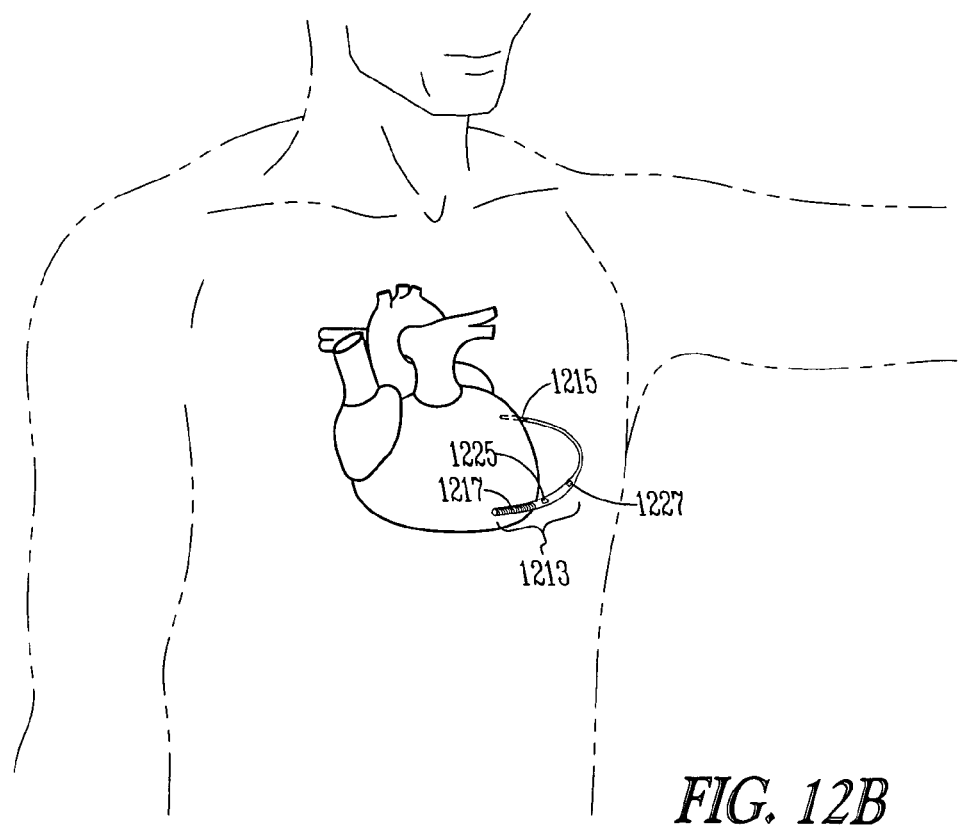

Other forms of electrodes include meshes and patches which may be applied to portions of heart 1105 or which may be implanted in other areas of the body to help "steer" electrical currents produced by IMD 1100. The present methods and systems will work in a variety of configurations and with a variety of electrodes. FIGS. 12A-B show an example of an IMD 1200 that does not use intravascular leads to sense cardiac signals. FIG. 12A shows that the IMD 1200 includes a thicker end 1213 to hold the power source and circuits. The IMD 1200 also includes electrodes 1225 and 1227 for remote sensing of cardiac signals. Cardioversion/defibrillation is provided through electrodes 1215 and 1217. FIG. 12B shows the positioning of the IMD 1200 within a patient.

Figure 13:
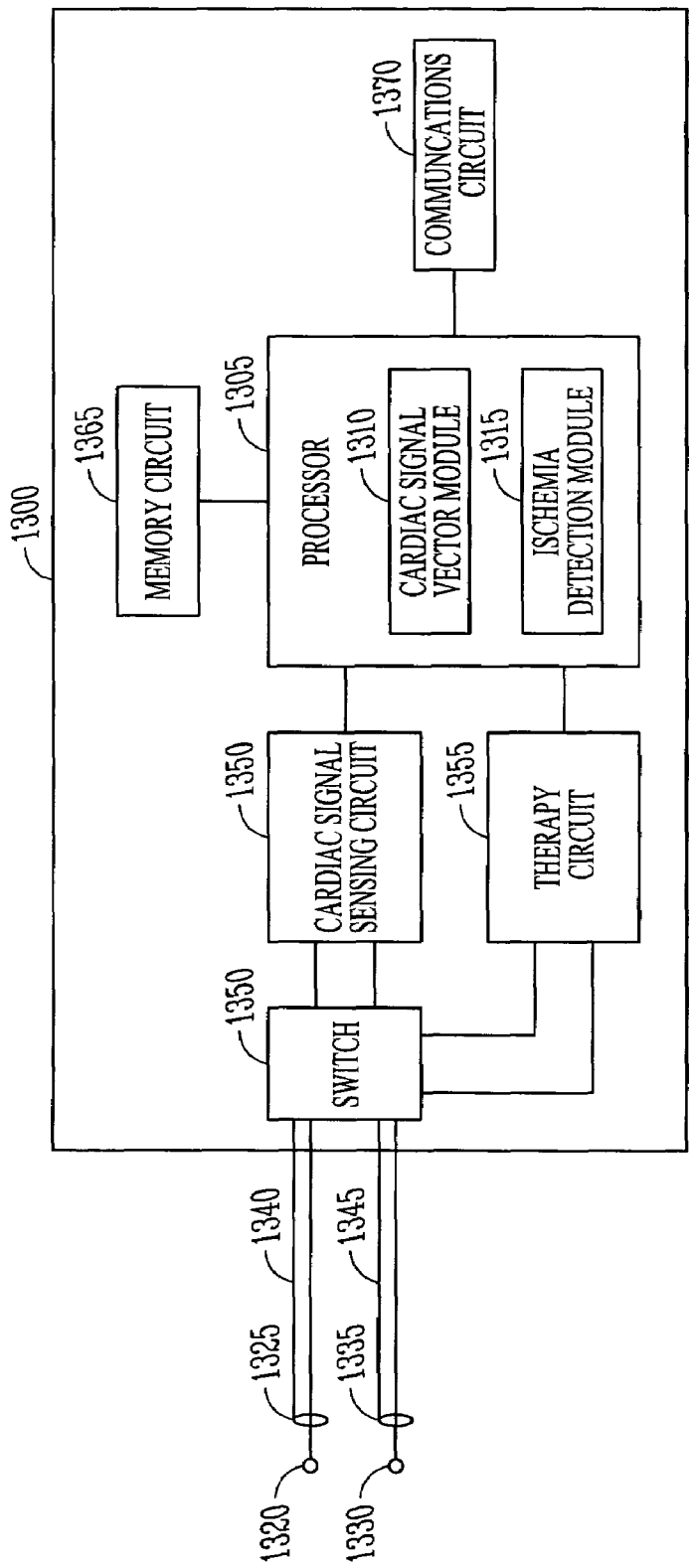
FIG. 13 is a block diagram of portions of an example of an IMD.

FIG. 13 is a block diagram of portions of an example of an IMD 1300 that includes a processor 1305 that in turn includes a cardiac signal vector module 1310 and an ischemia detection module 1315. The processor 1305 detects ischemia using any of the methods described herein. In some examples, the processor 1305 is included in a controller circuit that controls operation of the IMD 1300. Additionally, the IMD includes implantable tip electrodes 1320, 1330 and implantable ring electrodes 1325, 1335 provided on leads 1340 and 1345. The electrodes are adapted for spatial distribution within the subject. The leads in the example are bipolar leads for placement in an atrium or ventricle. Other electrode combinations are possible, such as additional lead electrodes, or can electrodes, or header electrodes.

The IMD 1300 also includes at least one cardiac signal sensing circuit 1350 in communication with the electrodes. The cardiac signal sensing circuit 1350 produces an electrical cardiac signal representative of cardiac activity of the subject. The cardiac signal sensing circuit 1350 senses electrical cardiac activity signals associated with an activation sequence of a heart. The activity signals propagate through the heart's electrical conduction system to excite various regions of myocardial tissue. The sensing circuit 1350 provides an electrical signal representative of such signals. Examples of cardiac signal sensing circuits 1350 include, without limitation, a subcutaneous ECG sensing circuit, an intracardiac electrogram (EGM) sensing circuit, and a wireless ECG sensing circuit. The wireless ECG circuit includes a plurality of electrodes adapted for placement to sense a cardiac signal approximating a surface ECG. The IMD 1300 includes a therapy circuit 1355 to provide electrical pacing or defibrillation therapy. IMD 1300 optionally includes a switch network 1360 to isolate the cardiac signal sensing circuit 1350 during therapy delivery.

In some examples, when the processor 1305 detects ischemia, the processor 1305 activates an alarm, such as a buzzer or other audible indication in the IMD 1300, to indicate that an ischemic event occurred.

In some examples, the IMD 1300 includes one or more other sensors, such as to measure intracardiac or trans-thoracic impedance, or blood pressure. In some examples, the processor 1305 uses at least one rule to blend the outputs of the various sensors and at least one signal separation measurement to make a decision as to whether a patient has experienced an ischemic event.

In some examples, the IMD 1300 includes a memory circuit 1365. The processor 1305 calculates trend data of measured subsequent changes from at least one baseline vector by any of the methods described herein and stores the trend data in the memory circuit 1365. In some examples, the processor 1305 establishes a value of the ischemia indication measured using the trend data and stores an ischemia indication using the trend data. In some examples, the IMD 1300 includes a communication circuit 1370 to communicate wirelessly with an external device. The indication of the ischemic event or an alarm can then be transmitted to a caregiver using the external device. The external device may receive an alarm status from the IMD 1300 when the IMD 1300 is next interrogated or by a communication originating from the IMD 1300. The alarm may be used to notify the patient, a caregiver, or both a patient and caregiver of the ischemic event.

Figure 14:
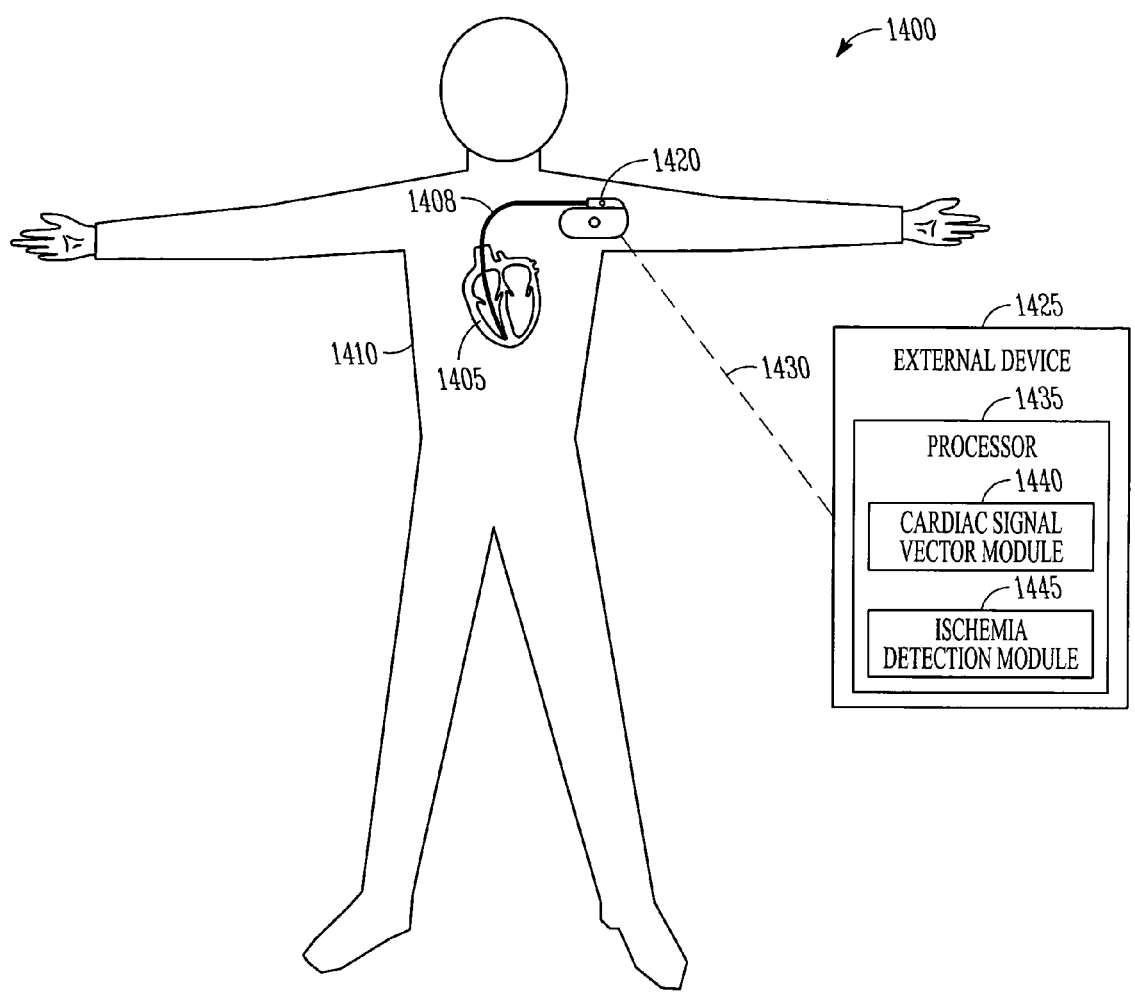
FIG. 14 illustrates portions of a system that includes an IMD coupled to a heart of a subject.

FIG. 14 illustrates portions of a system 1400 that includes an IMD 1420 coupled to heart 1405 of a subject 1410 via a lead 1408. The system 1400 further includes an external device 1425 that communicates wireless signals 1430 with the IMD 1420. In the system 1400, the external device 1425 instead of the IMD 1420 includes a processor 1435 that in turns includes a cardiac signal vector module 1440 and an ischemia detection module 1445. The IMD 1420 includes a plurality of implantable electrodes adapted for spatial distribution within the subject 1410, and at least one cardiac signal sensing circuit in communication with the electrodes. The cardiac signal sensing circuit produces an electrical cardiac signal representative of cardiac activity of the subject 1410. The IMD includes a controller circuit coupled to the cardiac signal sensing circuit to control IMD functions and a communication circuit coupled to the controller circuit. The IMD 1420 communicates information related to cardiac electrical signals with the external device 1425 and the processor 1435 in the external device 1425 detects ischemia using any of the methods described herein.

In some examples, the external device 1425 includes a display. This allows a caregiver to read a signal sampled after an ischemic event out from device memory and observe the event at a subsequent patient visit. An indication in the IMD is communicated to an external device to alert the caregiver of the event. Additionally, the external device 1425 displays a graph such as the graph in FIG. 5E to indicate the change in computed vectors. In some examples, an external device 1425 located somewhere other than in a clinic, such as in a patient's home, can read out and communicate the sampled signal to the caregiver's location for display. This monitoring identifies those patients that experience ischemia to a caregiver, allowing the caregiver to notify emergency personnel, or to make adjustments to parameters of a CFM device, or to adjust a patient's drug therapy.

Examples of the external device 1425 include an IMD programmer. In some examples, the external device 1425 is part of, or in communication with, a computer network such as a hospital computer network or the internet. An indication of the ischemic event or an alarm can then be transmitted to a caregiver using the network. An indication or alarm provided to the patient has further uses, such as to direct the patient to take a drug, adjust medication, or to seek immediate medical assistance. In some examples, the external device 1425 is in communication with a mobile telephone network. In some examples, the external device is a repeater that communicates wirelessly with the IMD 1420 and with a third device in communication with a network, such as a computer network or mobile telephone network.

Figure 15:
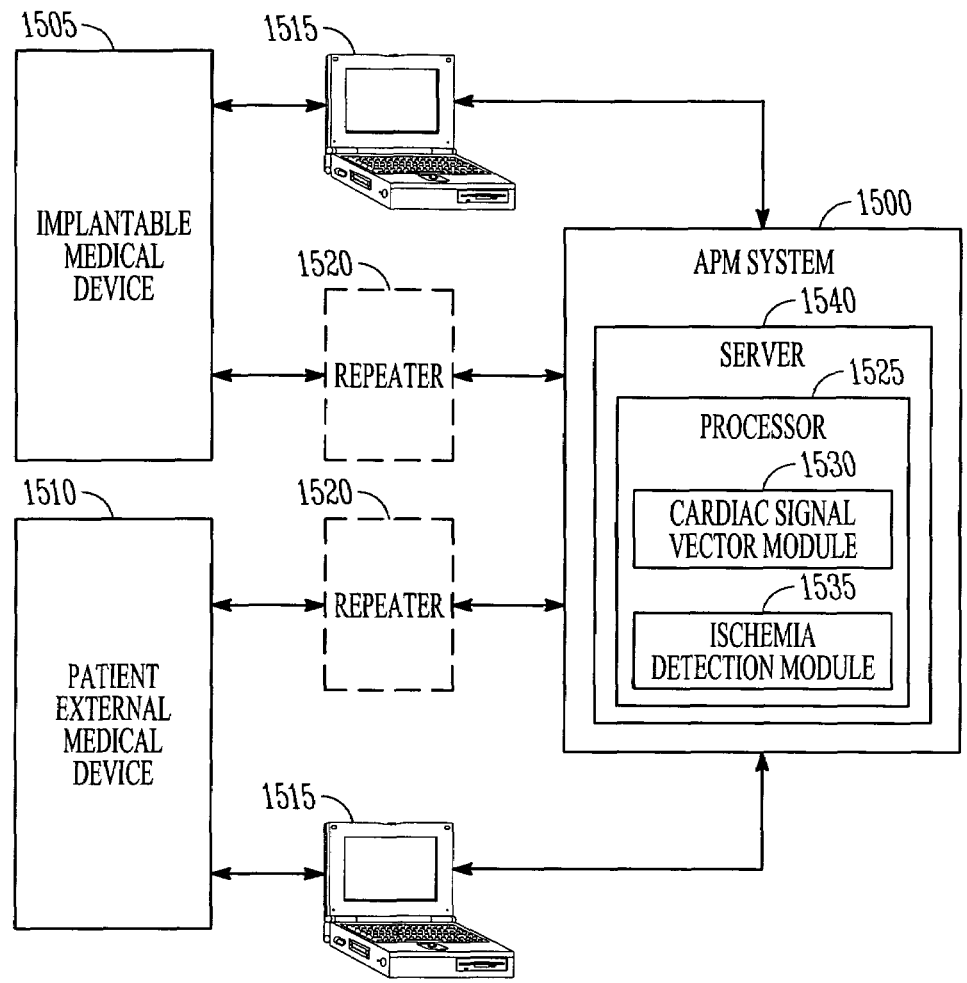
FIG. 15 shows a block diagram of medical devices in communication with an advanced patient management (APM) system.

FIG. 15 shows an example of medical devices that communicate with an advanced patient management (APM) system 1500. An APM system is a communication infrastructure that allows physicians and caregivers to remotely and automatically monitor, among other things, cardiac and respiratory functions of patients. The APM system also allows for remote and/or automatic adjusting of devices internal or external to a patient that provide patient therapy. The APM system 1500 communicates with either implantable medical devices 1505 or patient external medical devices 1510. Examples of a patient external device includes external patient monitoring and therapy delivery devices, including cardiac devices that include or work in coordination with neuro-stimulating devices. In some examples, the communication is through medical device programmers 1515 that the APM communicates with over a network. An IMD programmer 1515 communicates wirelessly with the IMD 1505. In some examples, the APM system 1500 communicate directly with the medical devices 1505, 1510 through repeaters 1520 that communicate wirelessly with the medical devices 1505, 1510 and the APM system 1500.

The processor of FIG. 10 can reside in the IMD 1505 or the external medical device 1510 or an IMD programmer 1515. FIG. 15 shows a processor 1525 having a cardiac signal vector module 1530 and an ischemia detection module 1535 included in an APM system server 1540. The IMD 1505 communicates information related to cardiac electrical signals with an external device such as a repeater 1520 or an IMD programmer 1515. The information is relayed to the APM system server 1540 over a network such as a computer network or a wireless communication network. The processor 1525 detects ischemia using any of the methods described herein. In some examples, the server 1540 initiates at least one dominant vector measurement. The measurement may be automatically triggered periodically, such as by a client running on the server 1540, or it may be initiated through the server 1540 by a user such as a clinician.

Noise may cause deviation of the ST or ST-T segment of the cardiac cycle, which may lead to false detections of ischemia from ECG or electrograms (EGM). One source of such is postural changes of a patient. The systems and methods described herein allow this noise to be attenuated or removed from measurements used to detect ischemia. This could remove ECG morphological variations due to noise such as postural change thereby reducing false-positives in measurements and improve specificity of ischemia detection. It is to be noted that the systems and methods described herein are applicable to remove sources of noise other than postural change noise and to remove noise from measurements other than ischemia measurements. The systems and methods can be used in any measurement using a dominant vector where the measured event affects a part of the cardiac cycle while the noise affects another part of the cardiac cycle or the entire cardiac cycle. A change in a first dominant vector will include a measured change that is of interest as well as measured noise. A change in a second dominant vector includes mostly only the measured noise. Forming a difference of the changes will result in a measurement that mostly includes the measured change that is of interest.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own.

What is claimed is:

1. A system comprising:
   a processor including:
      a cardiac signal vector module configured to measure, from an electrical cardiac signal, a first dominant vector corresponding to a direction and magnitude of maximum signal power of an ST-T first segment of at least one cardiac cycle of a subject and at least a second dominant vector corresponding to a direction and magnitude of maximum signal power of a P-QRS second segment of the cardiac cycle, wherein the P-QRS segment includes the P-wave and extends to and includes the S-wave; and
      an ischemia detection module configured to measure a change in the first dominant vector and the second dominant vector, to form a difference by subtracting a measured change in the second dominant vector from the measured change in the first dominant vector, and to declare whether an ischemic event occurred using the difference.

2. The system of claim 1, wherein the ischemia detection module reduces noise due to posture of the subject by the subtracting the measured change in the second dominant vector from the measured change in the first dominant vector.

3. The system of claim 1, wherein the cardiac signal vector module is further configured to establish first and second baseline vectors for the first and second dominant vectors, and wherein the ischemia detection module is further configured to measure a change in a dominant vector relative to a baseline vector.

4. The system of claim 3, wherein the ischemia detection module is further configured to:
   subtract the first baseline vector from a later-measured first dominant vector to obtain a first change representative of a change due to posture during the first segment;
   subtract the second baseline vector from a later-measured second dominant vector to obtain a second change representative of a change due to posture and ischemia during the second segment; and
   subtract the first change from the second change to obtain a third change representative of a change due to ischemia.

5. The system of claim 3, wherein the ischemia detection module is configured to measure a change in a dominant vector by measuring at least one of a change in angle, a change in magnitude, a variance of the angle or the magnitude, a power spectral density, a rate of change of the angle, a rate of change of the magnitude, and a rate of change of the variance of the angle or the magnitude.

6. The system of claim 3, wherein the processor is operable to calculate trend data of measured subsequent changes from at least one baseline vector, and wherein the system includes a memory circuit coupled to the processor to store the trend data.

7. The system of claim 6, further including an ischemia indicator stored in the memory circuit, wherein the processor is operable to establish a value of the ischemia indicator using the trend data.

8. The system of claim 1, wherein the ischemia detection module declares that an ischemic event occurred when the difference exceeds a specified threshold value.

9. The system of claim 8, wherein the ischemia detection module declares that an ischemic event occurred if the difference exceeds a specified threshold value in X of Y consecutive cardiac cycles, wherein X and Y are integers and X is less than or equal to Y.

10. The system of claim 1, wherein the processor is included in an implantable medical device (IMD) and wherein the IMD further includes:
    a plurality of implantable electrodes adapted for spatial distribution within the subject; and
    at least one cardiac signal sensing circuit in communication with the electrodes, the cardiac signal sensing circuit operable to produce the electrical cardiac signal representative of cardiac activity of the subject, and wherein the processor is coupled to the cardiac signal sensing circuit.

11. The system of claim 10, wherein the plurality of implantable electrodes includes at least a first electrode and a second electrode adapted for placement to sense a cardiac signal approximating a surface electrocardiogram (ECG).

12. The system of claim 1, further including:
    an implantable medical device (IMD) comprising:
       a plurality of implantable electrodes adapted for spatial distribution within the subject;
       at least one cardiac signal sensing circuit in communication with the electrodes, the cardiac signal sensing circuit operable to produce the electrical cardiac signal representative of cardiac activity of the subject;
       a controller circuit coupled to the cardiac signal sensing circuit; and
       a communication circuit coupled to the controller circuit; and
    an external device, wherein the IMD is operable to communicate information to the external device and wherein the processor is included in the external device.

13. The system of claim 12, wherein the external device includes an IMD programmer.

14. The system of claim 12, wherein the external device includes a display configured to display a change in at least one of a magnitude and a direction of a computed vector.

15. The system of claim 1, wherein the processor is configured to activate an alarm indicative of a deemed ischemic event.

16. The system of claim 1, further including:
an implantable medical device (IMD) comprising:
- a plurality of implantable electrodes adapted for spatial distribution within the subject;
- at least one cardiac signal sensing circuit in communication with the electrodes, the cardiac signal sensing circuit operable to produce the electrical cardiac signal representative of cardiac activity of the subject;
- a controller circuit coupled to the cardiac signal sensing circuit; and
- a communication circuit coupled to the controller circuit;

an external device, wherein the IMD is operable to communicate information to the external device; and a server in communication with a network, wherein the server includes the processor, and wherein the external device is operable to communicate with the server via the network.

17. The system of claim 16, wherein the server initiates at least one dominant vector measurement.

18. The system of claim 1, wherein the ischemia detection module is configured to deem whether an ischemic event occurred from whether the difference exceeds a specified threshold value in combination with a measured output provided from one or more sensors.

19. The system of claim 18, wherein the ischemia detection module is configured to deem whether an ischemic event occurred by blending the output provided by the censor and the difference according to at least one rule.

20. The system of claim 18, wherein the sensor includes at least one of a intracardiac impedance sensor, a transthoracic impedance sensor, and a blood pressure sensor.

* * * * *

UNITED STATES PATENT AND TRADEMARK OFFICE
CERTIFICATE OF CORRECTION

PATENT NO. : 7,567,836 B2  
APPLICATION NO. : 11/275800  
DATED : July 28, 2009  
INVENTOR(S) : Yi Zhang Page 1 of 1

It is certified that error appears in the above-identified patent and that said Letters Patent is hereby corrected as shown below:

On Sheet 14 of 16, Box 1370, in Figure 13, line 1, delete "COMMUNCATIONS" and insert -- COMMUNICATIONS --, therefor.

In column 1, line 13, delete "DETECTION"," and insert -- DETECTION", --, therefor.

In column 22, line 14, in Claim 19, delete "censor" and insert -- sensor --, therefor.

Signed and Sealed this

Sixth Day of October, 2009

David J. Kappos
*Director of the United States Patent and Trademark Office*